(12) United States Patent
Aliaga et al.

(10) Patent No.: US 9,659,351 B2
(45) Date of Patent: May 23, 2017

(54) DISPLAYING PERSONALIZED IMAGERY FOR IMPROVING VISUAL ACUITY

(71) Applicant: Purdue Research Foundation, West Lafayette, IN (US)

(72) Inventors: Daniel Gerardo Aliaga, West Lafayette, IN (US); Carlos Roberto Montalto Cruz, Seattle, WA (US); Ignacio Garcia Dorado, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 14/656,681

(22) Filed: Mar. 12, 2015

(65) Prior Publication Data

US 2015/0269434 A1 Sep. 24, 2015

Related U.S. Application Data

(60) Provisional application No. 61/951,995, filed on Mar. 12, 2014.

(51) Int. Cl.
*G06K 9/00* (2006.01)
*G06T 5/00* (2006.01)
*A61B 3/00* (2006.01)
*A61B 3/032* (2006.01)

(52) U.S. Cl.
CPC ............... *G06T 5/001* (2013.01); *A61B 3/00* (2013.01); *A61B 3/032* (2013.01); *G06T 5/003* (2013.01); *G06T 2207/20056* (2013.01)

(58) Field of Classification Search
CPC ........... G06T 2207/20056; G06T 5/001; G06T 5/003
See application file for complete search history.

(56) References Cited

U.S. PATENT DOCUMENTS

| | | | |
|---|---|---|---|
| 2003/0107703 A1* | 6/2003 | Cox ..................... | A61B 3/1015 351/159.21 |
| 2004/0263786 A1* | 12/2004 | Williams ............. | A61B 3/0025 351/246 |
| 2007/0222948 A1* | 9/2007 | Dai ...................... | A61B 3/1015 351/212 |

(Continued)

OTHER PUBLICATIONS

Vogel et al., Fast, Robust Total Variation-Based Reconstruction of Noisy, Blurred Images, 1998, IEEE Transactions on Image Processing, vol. 7, No. 6, pp. 813-824.*

(Continued)

*Primary Examiner* — Vu Le
*Assistant Examiner* — Guillermo Rivera-Martinez
(74) *Attorney, Agent, or Firm* — Purdue Research Foundation

(57) ABSTRACT

A method to generate an output image that improves observation of a target image viewed on a medium by an optical system is disclosed. The method includes receiving at least one target image by a processing system, receiving at least one parameter by the processing system, defining an error signal associated with the difference between calculated optical system observation of intermediate images and the at least one target image, minimizing the error signal, and generating an output image associated with the intermediate image having the minimized error.

12 Claims, 19 Drawing Sheets

(56) References Cited

U.S. PATENT DOCUMENTS

| | | | |
|---|---|---|---|
| 2010/0166332 A1* | 7/2010 | Lee | G06T 5/003 382/255 |
| 2011/0085741 A1* | 4/2011 | Zhang | G06T 5/003 382/255 |
| 2011/0091129 A1* | 4/2011 | Ichihashi | G06T 5/003 382/275 |
| 2011/0115934 A1* | 5/2011 | Wang | G06T 3/4076 348/222.1 |
| 2011/0149241 A1* | 6/2011 | Dai | A61F 9/00806 351/205 |

OTHER PUBLICATIONS

Combettes et al.,lmage Restoration Subject to a Total Variation Constraint, 2004, IEEE Transactions on Image Processing, vol. 13, No. 9,pp. 1213-1222.*
Aliaga, D., et al., A Virtual Restoration Stage for Real-World Objects. ACM Trans. Graph. 27, 5, Article 149 (Dec. 2008), 10 pages.
Alonso, M., et al., Pre-Compensation for High-Order Aberrations of the Human Eye Using On-Screen Image Deconvolution. Proceedings of the 25' Annual Inteerational Conference of the IEEE EMBS. Cancun, Mexico Sep. 17-21, 2003.
Alonso, M., et al., Howard: High-Order Wavefront Aberration Regularized Deconvolution for Enhancing Graphic Displays for Visually Impaired Computer Users. K. Miesenberger et al. (Eds.): ICCHP 2006, LNCS 4061, pp. 1163-1170, 2006.
Alonso, M., et al., Digital image inverse filtering for improving visual acuity for computer users with visual aberrations. Inverse Problems in Science and Engineering vol. 16, No. 8, Dec. 2008, 957-966.
Anstis, S. M., et al., A Craik-O'Brien-Cornsweet Illusion for Visual Depth. Vision Res. vol. 18, pp. 213-217, 1978.
Wang, Y., et al., A New Alternating Minimization Algorithm for Total Variation Image Reconstruction. Siam J. Imaging Sciences. 2008 Society for Industrial and Applied Mathematics. vol. 1, No. 3, pp. 248-272, 2008.
Beck, A. et al., Fast Gradient-Based Algorithms for Constrained Total Variation Image Denoising and Deblurring Problems. IEEE Transactions on Image Processing, Vol. 18, No. 11, 2419-2434, 2009.
Brown, M. S., et al., Image Pre-conditioning for Out-of-Focus Projector Blur. Proc. IEEE Conference on Computer Vision and Pattern Recognition (CVPR), New York, NY, vol. 2, pp. 1956-1963, 2006.
Chambolle, A., An Algorithm for Total Variation Minimization and Applications. Journal of Mathematical Imaging and Vision 20: 89-97, 2004.
Chan, T. F., et al., A Nonlinear primal-dual method for total variation-based image restoration. SIAM J. Sci. Comput., vol. 20, 1964-1977, 1999.
Veeraraghavan, A., et al., Dappled Photography: Mask Enhanced Cameras for Heterodyned Light Fields and Coded Aperture Refocusing. ACM Transactions on Graphics, vol. 26, No. 3, Article 69, Publication date: Jul. 2007.
Villegas, E. A., et al., Optical Quality of the Eye in Subjects with Normal and Excellent Visual Acuity. Investigative Ophthalmology & Visual Science, Oct. 2008, vol. 49, No. 10, 4688-4696.
Didyk, P., et al., A Perceptual Model for Disparity. Acm TRANSACTIONS on Graphics (TOG)—Proceedings of ACM SIGGRAPH 2011, vol. 30 Issue 4, Jul. 2011, Article No. 96.

Zhang, L., et al., Projection Defocus Analysis for Scene Capture and Image Display. Projection Defocus Analysis for Scene Capture and Image Display, ACM Trans. on Graphics, 2006.
Dunaway, D., et al., Worldwide Distribution of Visual Refractive Errors and What to Expect At a Particular Location. Presentation to the International Society for Geographic and Epidemiologic Ophthalmology, 2006.
Hampson, K. M. (2008) Adaptive optics and vision, Journal of Modern Optics, vol. 55, No. 21, Dec. 10, 2008, 3425-3467.
Huang, F., et al., Correcting for Optical Aberrations using Multilayer Displays. Correcting for optical aberrations using multilayer displays. ACM Transaction on Graphics, 31, 6, Article No. 185, 2012.
Joshi, N., et al., Image Deblurring and Denoising using Color Priors. Image deblurring and denoising using color priors. In Proceedings of the IEEE Computer Vision and Pattern Recognition, 1550-1557, 2009.
Krishnan, D., et al., A primal-dual active-set algorithm for bilaterally constrained total variation deblurring and piecewise constant Mumford-Shah segmentation problems. Adv Comput Math (2009) 31:237-266.
Krishnan, D., et al., Fast Image Deconvolution using Hyper-Laplacian Priors. Advances in Neural Information Processing Systems 22, 8 pages, 2009.
Yuan, L., et al., Progressive Inter-scale and Intra-scale Non-blind Image Deconvolution. ACM Transactions on Graphics, vol. 27, No. 3, Article 74, Publication date: Aug. 2008.
Lakshminarayanan, V., New Results in Biomedical Image Processing. International Conference on Fiber Optics and Photonics © OSA 2012.
Legge, G. E., et al., Psychophysics of Reading—I. Normal Vision. Vision Res. vol. 25(2), pp. 239-252, 1985.
Rusinkiewicz, S., et al., Exaggerated Shading for Depicting Shape and Detail. ACM Transactions on Graphics, 25, 3, 1199-1205, 2006.
Mohammadpour, S., et al., A Pre-compensation algorithm for different optical aberrations using an enhanced wiener filter and edge tapering. In IEEE Int'l Conf. on Information Science, Signal Processing and their Applications (ISSPA), 935-939, 2012.
Thibos, L. N., et al., Standards for Reporting the Optical Aberrations of Eyes. J Refract Surg 2002;18:S652-S660.
Oyamada, Y., et al., Focal Pre-Correction of Projected Image for Deblurring Screen Image. In IEEE Conference on Computer Vision and Pattern Recognition, 2007.
Rudin, L., I., et al., Nonlinear total variation based noise removal algorithms. Physica D 60 (1992) 259-268.
Pamplona, V. F., et al., Tailored Displays to Compensate for Visual Aberrations. ACM Trans. Graph. 31, 4, 81:1-81:12, 2012.
Peli, E., et al., Image Enhancement for Impaired Vision: The Challenge of Evaluation. Int J Artif Intell Tools. Jun. 2009 ; 18(3): 415-438.
Lee, B., et al., Characterization of Red-Green and Blue-Yellow Opponent Channels. Journal of Imaging Science and Technology® 51(1): 23-33, 2007.
Ritschel, T., et al., 3D Unsharp Masking for Scene Coherent Enhancement. ACM Trans. on Graphics, 27(3), 8 pages, 2008.
Raskar, R., et al., Shader Lamps: Animating Real Objects With Image-Based Illumination. In Proceedings of the 12th Eurographics Workshop on Rendering Techniques, London, UK, 89-102, 2001.
Raskar, R., Agrawal, A., and Tumblin, J. 2006. Coded exposure photography: motion deblurring using fluttered shutter. ACM Trans. Graph. 25, 3, 795-804, 2006.
Huang, F., et al., Eyeglasses-free Display: Towards Correcting Visual Aberrations with Computational Light Field Displays. ACM Transaction on Graphics, Aug. 2014.

* cited by examiner

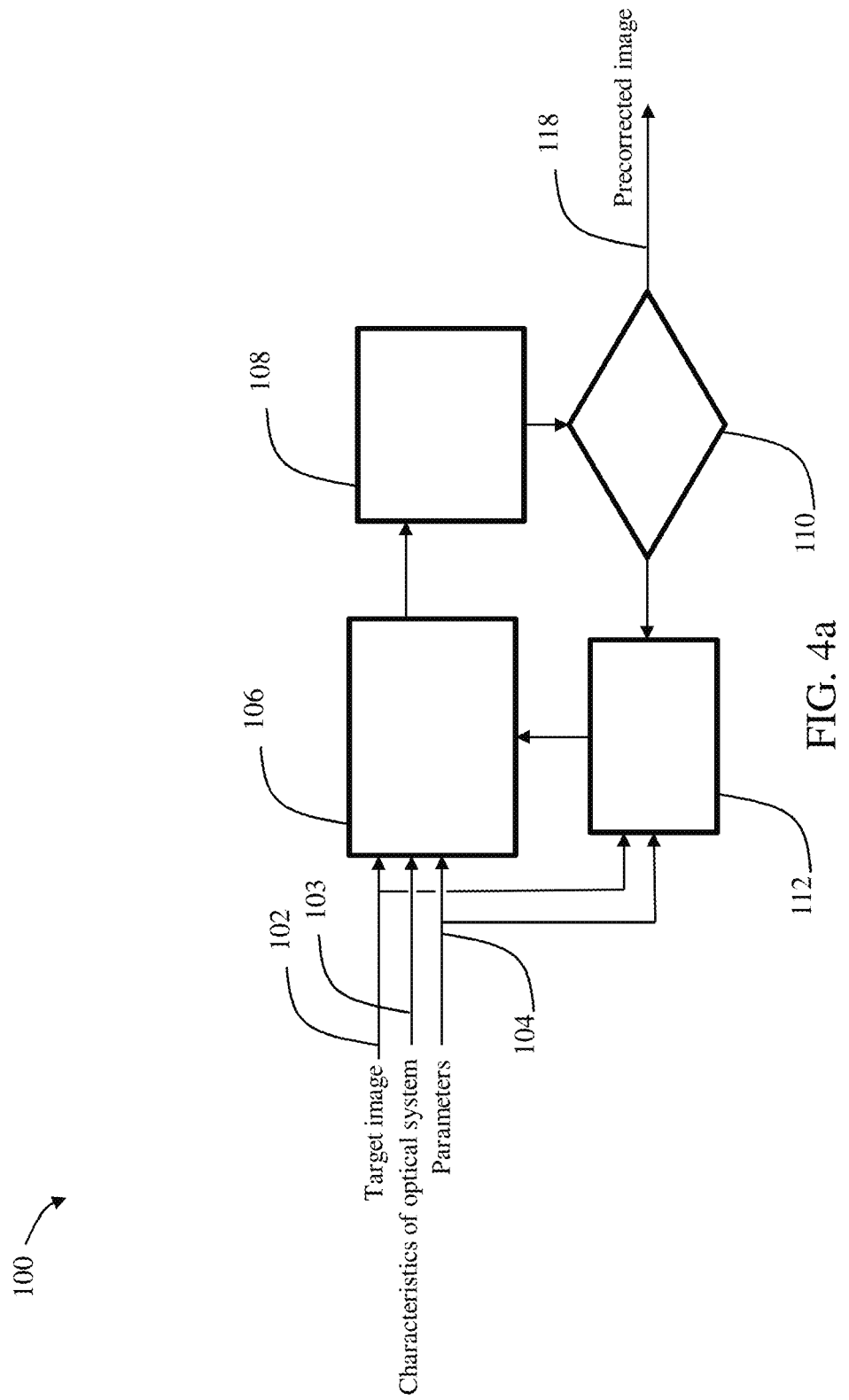

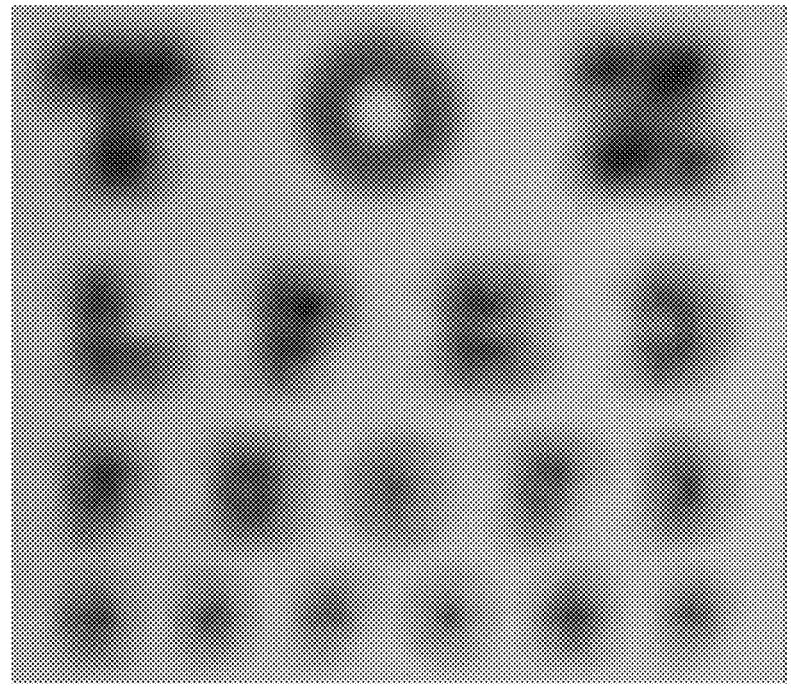
Blurred target image
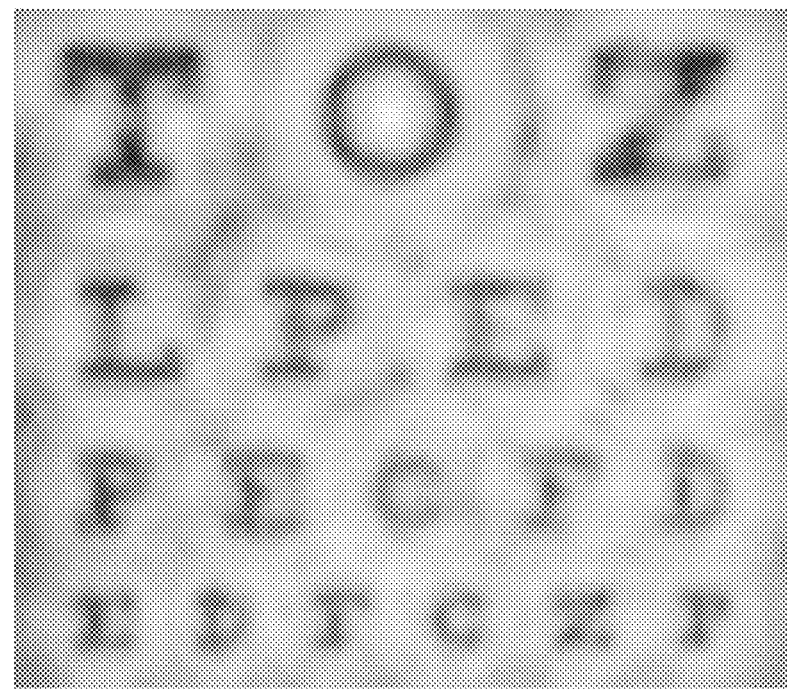
Captured precorrected image
FIG. 11

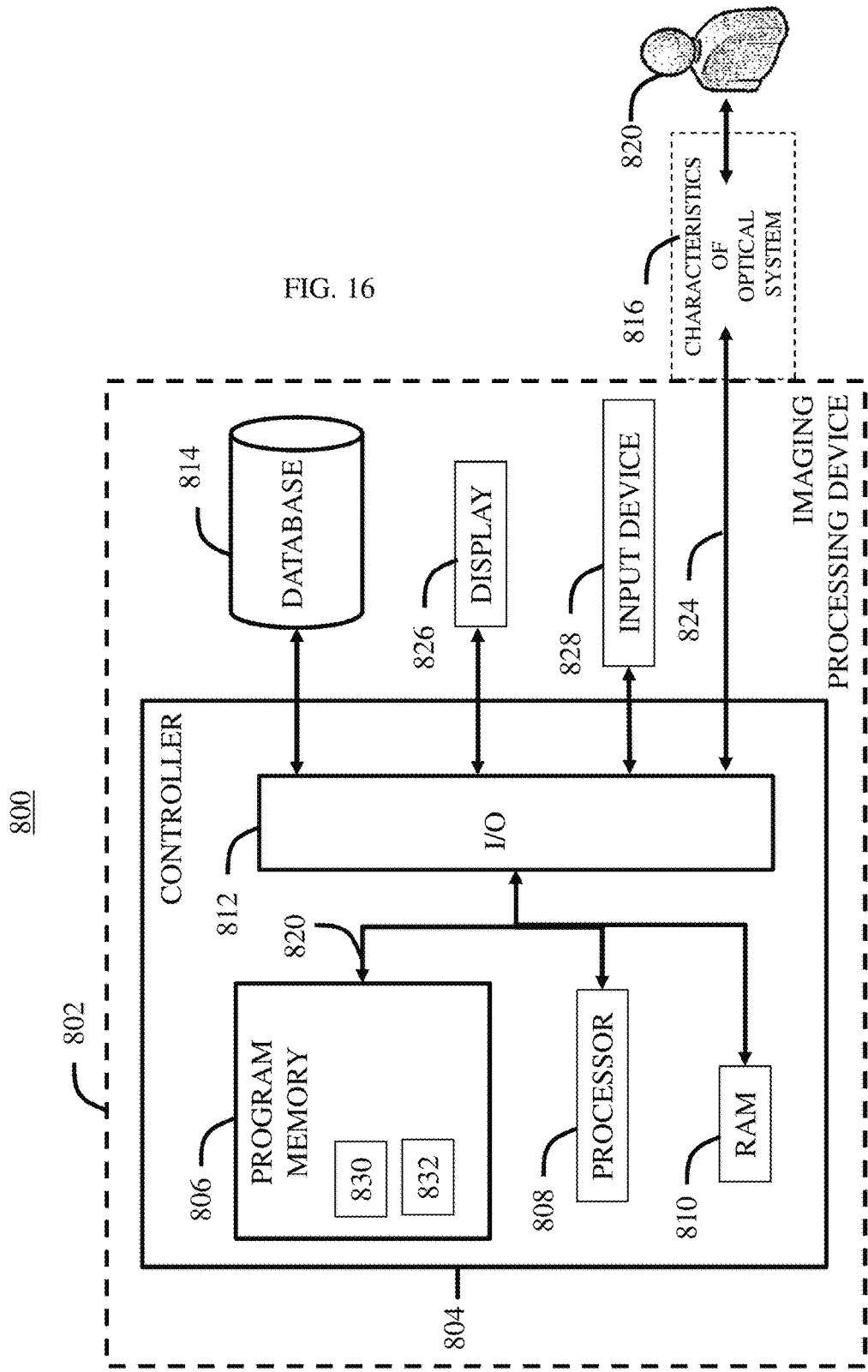

DISPLAYING PERSONALIZED IMAGERY FOR IMPROVING VISUAL ACUITY

CROSS-REFERENCE TO RELATED APPLICATIONS

The present U.S. patent application is related to and claims the priority benefit of U.S. Provisional Patent Application Ser. No. 61/951,995, filed Mar. 12, 2014, the contents of which are hereby incorporated by reference in their entirety into the present disclosure.

GOVERNMENT SUPPORT CLAUSE

This invention was made with government support under CNS0913875 awarded by the National Science Foundation. The government has certain rights in the invention.

TECHNICAL FIELD

The present disclosure relates to improving visual acuity and, more particularly, to techniques for producing imagery with improved sharpness and contrast for individuals having refractive vision problems.

BACKGROUND

This section introduces aspects that may help facilitate a better understanding of the disclosure. Accordingly, these statements are to be read in this light and are not to be understood as admissions about what is or is not prior art.

A significant fraction of the population suffers from refractive errors in their visual system. Correction is commonly in the form of eyeglasses or contacts having the needed optical correction for an individual.

One alternative explored in prior art is developing custom display hardware for providing improved sharpness and focus for observers. On the one hand, adaptive optics has emerged as a field that attempts to measure, in real-time, optical aberrations using custom refractive and reflective hardware. On the other hand, lightfield displays have recently been proposed to improve static long-term optical aberrations, such as defocus and astigmatism in human vision systems. An example is a lightfield display that dynamically adapts its content to the observer's specific condition, causing it to appear focused despite of his/her refractive vision problem. Presented prototypes can show imagery for a region of a person's field-of-view (FOV). Others have proposed multi-layer display hardware solutions that also yield imagery appearing sharper for viewers. Both techniques typically require the viewer to be carefully tracked or kept in a fixed position.

Referring to FIG. 1a, a block diagram denoting a typical optical system. An image is presented to the normal optical system which is processed by the system and generates a perceived image. Referring to FIG. 1b, an optical system with aberrations is depicted. Similarly, the image is presented to the system and a perceived image is thereby generated. However, the perceived image may include a variety of issues, e.g., lack of focus, blurriness. To exemplify this situation, suppose a subject with hyperopia is viewing the image in 1b; hyperopia, or farsightedness, refers to situations in which a subject cannot focus on nearby objects. The image presented is perceived as blurry. The aberration (in this case hyperopia) can be modeled as a convolution (FIG. 1c) of the original image as provided to the normal optical system. That is, the optical system with aberrations is equivalent to the normal optical system with the convolution block. Corrections can be based on a deconvolution of the image prior to it being presented to the optical system with aberrations (identified as pre-correction). Deconvolution is an operation to reverse the effect of convolution. Hence, the deconvolution process substantially cancels the aberration (i.e., convolution process) resulting in an improved perceived image (FIG. 1d).

An alternative method to hardware-based solutions is software-only approaches which in general use some form of deconvolution (note: some of the aforementioned custom display hardware may also use a form of deconvolution). Direct deconvolution methods (e.g., inverse filtering) are sensitive to noise in the data and impulse response, typically referred to as the system's point-spread-function (PSF). To improve upon this limitation, constraints are applied to an iterative deconvolution process (e.g., Weiner filtering or van Cittert's method). One common objective is to use constraints to regularize deconvolution by adding terms to the optimization in order to find a solution with desirable properties (i.e., low level of noise). A technique known as total variation (TV) based deconvolution is another form of regularized deconvolution that has been shown both experimentally and theoretically to be able to find (i.e., preserve) sharp edges in the solution image. The regularization term often includes the total variational norm of the optimized variable and at least one weight parameter.

The aforementioned deconvolution techniques are usually used for tasks where the solution image (i.e., the deconvolved image) has pixel values similar to those of the target image. However, the pixel values of a typical prior art approach pre-corrected image may not be in a fixed and valid pixel value range (e.g., [0.0, 1.0]). As a solution, techniques in prior art bring all pixel values computed by the deconvolution into a valid range by either clamping or re-scaling after the deconvolution computation. A consequence of this is very low contrast and potentially significant ringing in the imagery perceived by an observer. Ringing implies oscillations in image intensity appearing around sharp edges in the visual content. The rings emanate from such edges and appear essentially on top of other content producing a distracting visual artifact.

To illustrate previous approaches, FIG. 2 shows several representative solutions under the same amount of −2.5 D of defocus blur observed at 3 meters. Previous methods use either inverse Fourier transform or Weiner filtering with pixel values clamped or rescaled to the valid range (e.g., [0.0, 1.0]). Some methods perform additional denoising schemes or edge tapering as a post-process to reduce ringing—the results are slightly improved. The first and second columns of FIG. 2 show original and blurred images. The blurred images represent the images perceived by an optical system with aberrations. The third column contains precorrected images (i.e., images that have gone through some form of deconvolution and are ready to be presented to the optical system with the associated aberrations). The fourth and fifth columns are the synthetically convolved precorrected images as a representation of perceived images by the optical system with aberrations of the precorrected images and camera-captured pictures of the precorrected images under −2.5 diopters of blur; the blur is generated by physically added a premeasured lens in front of an otherwise focused camera. The purpose of showing the synthetically convolved images separate from the captured images is that synthetically convolved images may include physically unattainable pixel values (e.g., negative values, or values exceeding the maximum pixel value). Therefore, the captured images represent more realistic perceived images of the precorrected images.

The three rows of FIG. 2 are representative ideal results from the aforementioned methods using Wiener filtering. In the first row, the precorrected image computed by Weiner filtering has a dynamic range of [−19, +19] (note: the image that is presented is implicitly rescaled to [0.0,1.0]). This experiment was also repeated using a standard TV-based deconvolution and the result is similar. In the second and third rows, the dynamic range of the precorrected image is limited to [−9, +9] and to [−0.015, 0.985], respectively. In all rows, the convolved precorrected image is computed synthetically and thus pixel values outside [0.0, 1.0] can be used. The results are good though at lower contrast as the pixel range of the precorrected image is reduced. However, the captured precorrected images demonstrate how such pixel values cannot be used by a physical system. It should be noted that the third row is effectively the single layer solution implemented by prior art methods.

Therefore, there is an unmet need to provide a method and a system that can overcome the shortcomings of the deconvolution solutions provided in the prior art.

SUMMARY

A method to generate an output image that improves observation of a target image viewed on a medium by an optical system is disclosed. The method includes receiving at least one target image by a processing system, receiving at least one parameter by the processing system, defining an error signal associated with the difference between calculated optical system observation of intermediate images that are generated by the processing system and the at least one target image, where a first intermediate image is generated based on a bounded total variation deconvolution that is based on one or more characteristics associated with the optical system and the at least one parameter. The method further includes minimizing the error signal by altering the intermediate images based on changes to one or more characteristics associated with the intermediate images and the at least one parameter, resulting in an intermediate image associated with an error at or below a threshold, and generating an output image associated with the intermediate image having the minimized error. A calculated optical system observation of the output image generates a higher quality as compared to a calculated optical system observation of the at least one target image including more-sharp, less blurry, less out-of-focus, and combinations thereof.

An image improvement system is also disclosed. The system includes an input channel that is configured to receive at least one target image, and a processor. The processor is configured to receive at least one target image by a processing system, receive at least one parameter by the processing system, define an error signal associated with the difference between calculated optical system observation of intermediate images that are generated by the processing system and the at least one target image, where a first intermediate image is generated based on a total variation deconvolution that is based on one or more characteristics associated with the optical system and the at least one parameter. The method further includes minimizing the error signal by altering the intermediate images based on changes to one or more characteristics associated with the intermediate images and the at least one parameter, resulting in an intermediate image associated with an error at or below a threshold, and generating an output image associated with the intermediate image having the minimized error. A calculated optical system observation of the output image generates a higher quality as compared to a calculated optical system observation of the at least one target image including more-sharp, less blurry, less out-of-focus, and combinations thereof. The system further includes an output channel that is configured to output the output image.

Another image improvement system is also disclosed. The system includes an input channel that is configured to receive at least one target image, and a processor. The processor is configured to receive at least one target image by a processing system, receive at least one parameter by the processing system, define an error signal associated with the difference between calculated optical system observation of intermediate images that are generated by the processing system and the at least one target image, where a first intermediate image is generated based on a bounded deconvolution that is based on one or more characteristics associated with the optical system and the at least one parameter. The method further includes minimizing the error signal by altering the intermediate images based on changes to one or more characteristics associated with the intermediate images and the at least one parameter, resulting in an intermediate image associated with an error at or below a threshold, and generating an output image associated with the intermediate image having the minimized error. A calculated optical system observation of the output image generates a higher quality as compared to a calculated optical system observation of the at least one target image including more-sharp, less blurry, less out-of-focus, and combinations thereof. The system further includes an output channel that is configured to output the output image.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein:

FIG. 4a is a block diagram representing a system and a process according to the present disclosure.

FIG. 11 represents a portion of typical Snellen Chart is provided to estimate visual acuity.

FIG. 16 is an exemplary block diagram illustrating various components used in implementing an example embodiment of the techniques discussed herein.

Figure 1A:
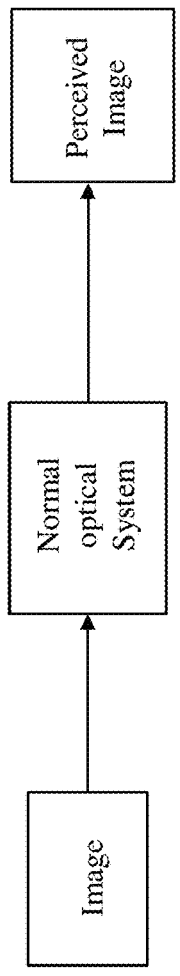
FIGS. 1a, 1b, 1c, 1d are block diagrams depicting observation of an image by an optical system, an optical system with aberrations, aberrations modeled as a convolution, and prior art methods of correcting for the aberrations by providing a precorrected image to account for the aberrations.
Figure 1B:
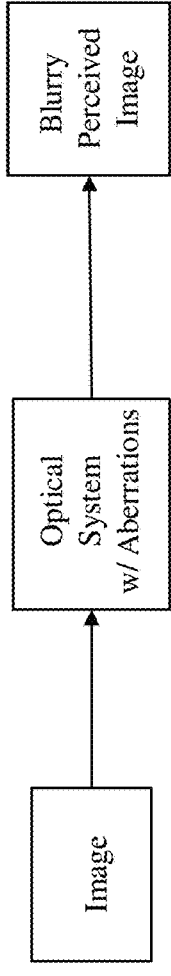
Figure 1C:
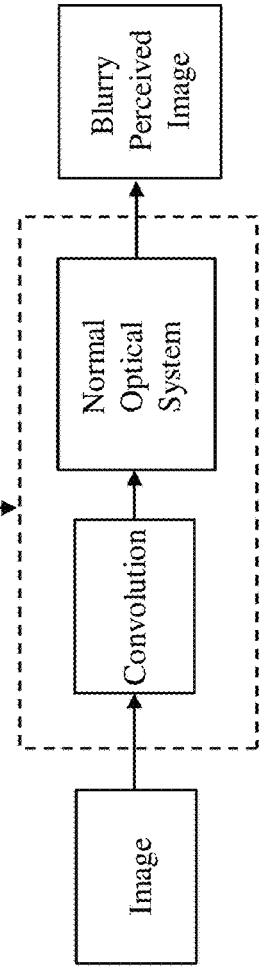
Figure 1D:
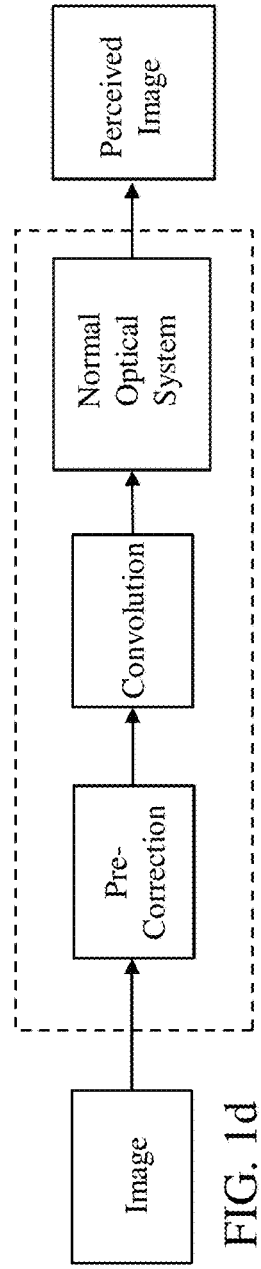

The attached drawings are for purposes of illustration and are not necessarily to scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present techniques provide a personalized computational method that modifies images to improve sharpness and contrast for observers with unaided eyes (e.g., no glasses, contacts, nor head-mounted displays). The techniques are useful for observers with refractive vision problems or for observers with normal (or corrected) vision and further for improving sharpness and contrast (e.g., for distant reading of signs or small nearby details). Moreover, the computed (precorrected) image can be viewed on any type of display (e.g., a computer screen, mobile device screen), with a projector, or on printed media so that upon direct observation it appears sharper and/or with equal or higher contrast than viewing the original unprocessed (target) image.

Figure 3:
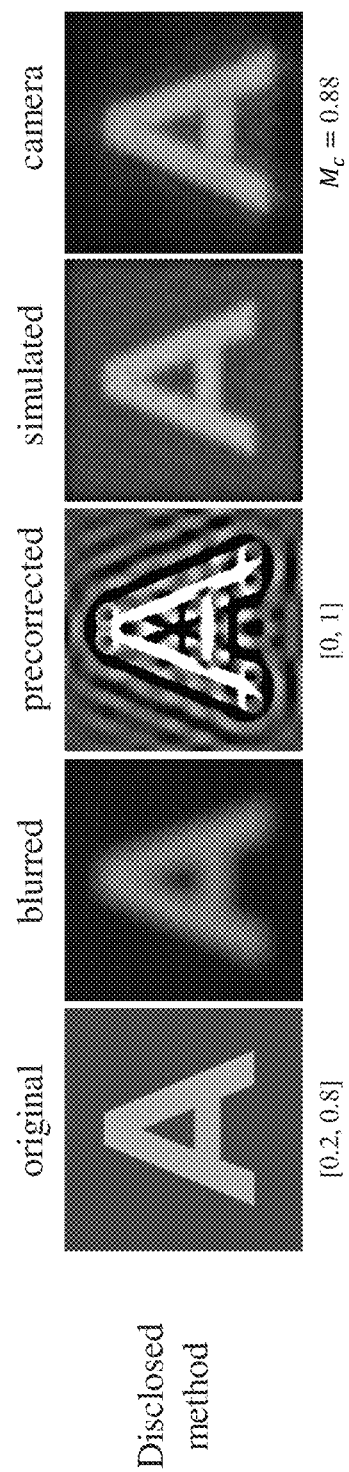
FIG. 3 is a schematic representation of the letter "A" as provided in an original target image, a calculated blurred image of an optical system with an aberration of the target image, a precorrection of the target image based on a software approach according to the teachings of the present disclosure, a calculated image of the optical system with the aberration of the precorrected image, and a captured image by a camera of the precorrected image.

FIG. 3 gives a prelude to the technique according to the present disclosure. In particular, the precorrected image is directly optimized within the [0.0, 1.0] range. The synthetically convolved precorrected image and the captured precorrected image both show notably improved contrast as opposed to the previous rows. The figure shows the Michelson contrast ratio $M_c$ (i.e., difference of maximum and minimum contrasts divided by the sum of maximum and minimum contrast ratios).

Referring to FIG. 4a, a block diagram is depicted according to the teachings of the present disclosure. A processing system 100 is depicted in FIG. 4a. The system 100 includes provisions for receiving at least one target image 102, one or more characteristics associated with the optical system 103, and at least one parameter 104. This target image 102 may be any content, for example, an image, video, font, visual digital content, or combinations thereof. Each target image 102 includes at least one channel of information (e.g., grayscale, color, or multichannel imagery). An amount of visual ringing is associated with image intensity oscillations surrounding contours in these channels of information of an image. Examples of a medium include, but are not limited to, an electronic display device, printed media, physical surface, projection onto a physical surface, or combinations thereof. The at least one parameter 104 (with an associated weight) is associated with one or more parts of the target image 102, and further to any image described. The one or more characteristics associated with the optical system 103 defines a point spread function, or other mathematically equivalent representation of an imaging capability of an eye's optical system; which includes an optical transfer function. In addition, the parameters 104 may be related to measurements of visual sharpness, contrast ratio, dynamic range, or visual ringing. Referring still to FIG. 4a, an error signal is associated with the difference between calculated optical system observation (i.e., convolution) 108 of intermediate images that are generated by the processing system and the target image 102. The first intermediate image is generated by block 106 based on i) a total variation deconvolution, ii) bounded deconvolution, or iii) bounded total variation deconvolution that is based on one or more characteristics associated with the optical system and the at least one parameter. One or more intermediate images (or intermediate computational results) may be generated by the processing system. Where at least one intermediate image is based on the target image, the error signal is minimized by altering one or more of the intermediate images based on one or more of the parameters 104, the target image 102, or by selecting from a precomputed set of intermediate images (that is, from the one or more intermediate images) as performed in parameter change block 112. These intermediate images have pixel values within a bounded value range during the error minimization and are substantially the same in size as the size of the target image, and the error minimization alters the one or more intermediate images, the values of the parameters 104, and combinations thereof. For example, altering the visual ringing in the areas of most contrast change in the one or more channels of information of an intermediate image may improve sharpness of the image generated by the optical system using the intermediate image. An output image associated with an intermediate image with the least error is then generated and becomes the precorrected image 118.

Specifically, the received target image 102 and the parameter 104 are provided to a convolution/deconvolution block 106. The deconvolution block 106 can operate based on bounded total variation deconvolution principals. The output of the convolution/deconvolution block 106 and target image 102 are provided as input to a block 108. The block 108 calculates the optical system's observation and provides this and the target image 102 to the block 110. The block 110 checks for error as compared to the target image. If the error is not at or below a predetermined threshold (which can also be provided as a parameter 104) the parameter change block 112 adjusts parameters associated with the image (e.g., contrast ratio, ringing parameters, deconvolution parameters). The parameters are fed to the convolution/deconvolution block 106. The output of the determination block 110 represents the precorrected image 118.

Bounded Deconvolution:

Bounded deconvolution is a form of regularized deconvolution, where the solution of the optimization is one that contains pixel values within a given range. As discussed above, the deconvolution approaches in prior art use pixel-value truncation and rescaling to bring the solution of a standard regularized deconvolution into a desired pixel range after the optimization; hence, the truncated or rescaled solutions do not minimize the model being optimized. At first sight, the problem of generating a precorrected image may appear to be an application of image deconvolution to the target image. In practice, however they are significantly different. The optimal solution of standard deblurring has pixel values similar to those of the blurred image (i.e., the solution pixels are within a valid pixel value range). However, the mathematical optimal solution for a precorrected image, that upon blurring becomes sharp (the target image), is usually very dissimilar to the target image (i.e., the pixels are outside valid pixel value range). In fact, it often contains pixels with negative and very large intensity values which are not suitable for a computer display or printed media.

Instead, the bounded deconvolution of the present disclosure uses regularization terms in the minimization to obtain the solution that minimizes the model of deconvolution within the desired pixel range. The optimization process uses projection-based methods during each iteration to constrain pixel range. There are several implementations of bounded deconvolution (e.g., iterative shrinking/thresholding (IST) methods, alternate direction method of multipliers (ADMM), etc.).

Total Variation Deconvolution

The following provides an exemplary description of a Total Variation Deconvolution of a given image c with a given kernel K. Other implementations are possible as would be known to a person skilled in the art. A Total Variation Deconvolution minimizes a functional that consists in two terms. The first term of the functional is the L2 norm of the difference between the convolution of the kernel K with the image d and the image c, this is called the deconvolution term. The second term is the product of a non-negative parameter s with the total variation norm of the image d, this is called the regularization term. The minimization of the deconvolution term finds an image d, such that the convolution of d with the kernel K is close to the image c. We say that two images are close to each other if the L2 norm of their difference is small. The minimization of the regularization term finds an image d with no change in contrast. In a Total Variation Deconvolution all terms are minimized simultaneously. This has the effect of obtaining an image d with two fundamental properties: (i) the convolution of d with the kernel K is close to the image c; and (ii) the contrast change of d is small. The parameter s in the second term allows to trade off the effect of the first and second terms. For example, smaller values of s give an image d whose convolution with the kernel K is close to a, but with large variations in contrast; using large values of s give an image d with small variations in contrast but whose convolution with the kernel K might not be close to c. This ability of controlling the contrast variation of the solution provides a good method of restricting the ringing of the solution.

Having a technique that quantitatively controls the contrast variation of the solution in a deconvolution process allows obtaining images with desired visual properties. For instance, images with high contrast variation present visual artifacts while very low contrast variation lacks image content information. The parameter s in a Total Variation Deconvolution allows finding a balance between visual artifacts and lack of content. The disclosed method obtains the solution of standard deconvolution by using the value of s=0 in the second term, this solution presents undesired visual artifacts as compared with a Total Variation Deconvolution method. Total Variation Deconvolution is a significant improvement over normal deconvolution because instead of having only one solution with strong visual artifacts it obtains a broad set of solutions with better visual properties.

Bounded Total Variation Deconvolution

The disclosed method uses a Bounded Total Variation Deconvolution, i.e., a Total Variation Deconvolution optimize the solution within a pixel interval value (e.g., in the range [0.0, 1.0]). The coupling of bounded deconvolution with Total Variation regularization generates precorrected images that exhibit limited amount of ringing and sharp edges, altogether yielding improved results when compared with previous works. Moreover, being able to optimize precorrected images with a pixel interval value guarantees the possibility of displaying the solution.

In comparison to previous works, the presented techniques may (i) provide naked-eye color viewing that yields improved sharpness despite the observer's refractive vision problems, (ii) offer high contrast, (iii) do not require glasses, contacts, or custom hardware (i.e., works with the unaided viewing of either current displays or printed content), and (iv) does not severely restrict observer movement, v) yield sharpness for high aberration levels (i.e., it has been tested for up to six diopters of myopia or hyperopia).

Precorrection Pipeline

Figure 4B:
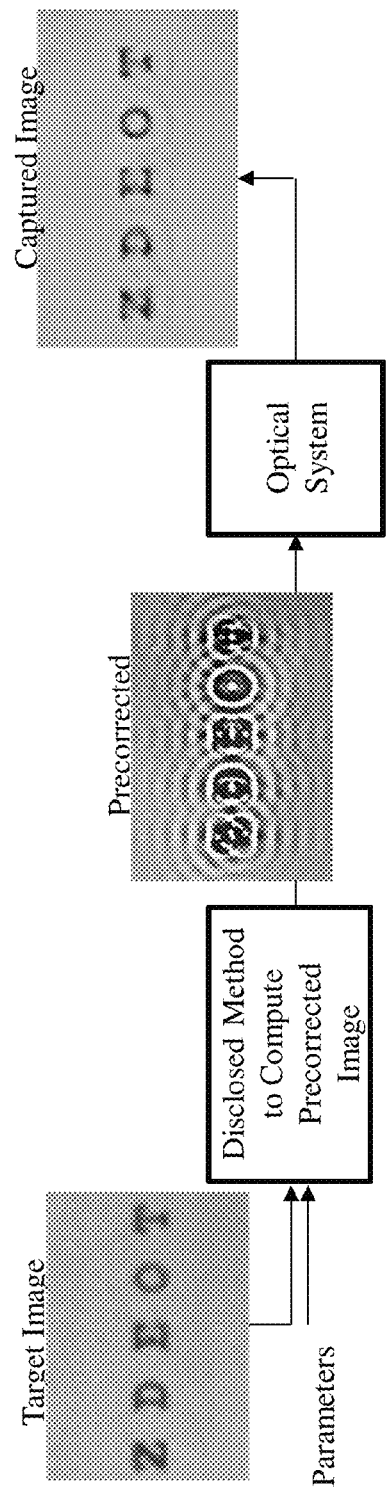
FIG. 4b is schematic representation of a target image, precorrection of the target image as provided by the present disclosure, and a calculated version of the observation of the precorrected image by the optical system with aberrations.
Figure 4C:
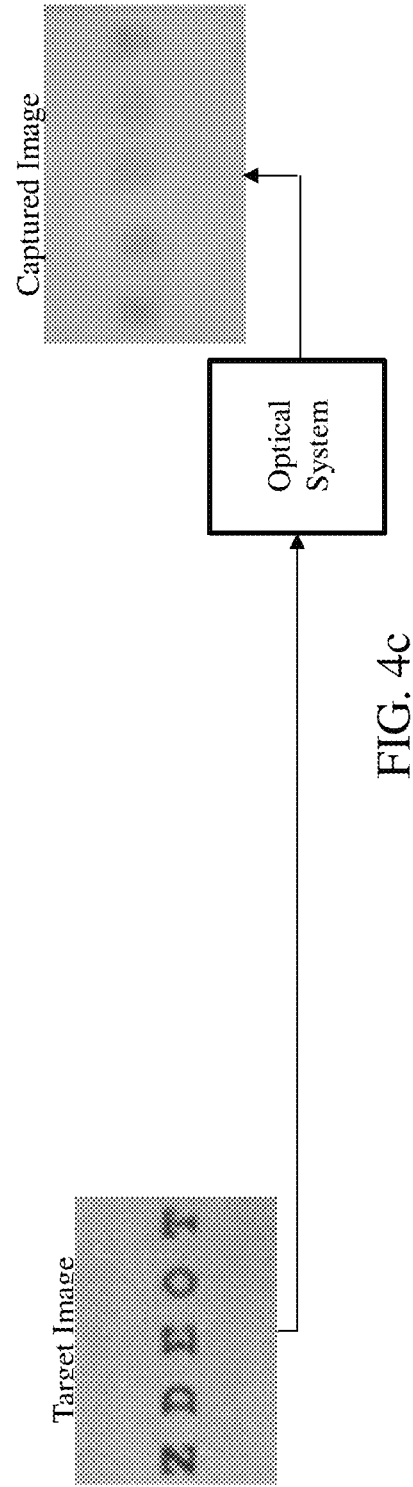
FIG. 4c is schematic representation of a target image and a calculated version of the observation by the optical system of the target image with aberrations.

Referring to FIGS. 4b and 4c, results of the application of the method according to the present disclosure is provided, and which results are compared with an optical system having an aberration but without the use of the method of the present disclosure. According to FIG. 4b, a target image is provided to a precorrection system according to the present disclosure. The target image is manipulated by the system to generate a precorrected image which is then provided to the optical system with aberrations. A simulated version is then captured by a camera to show the effect of the system as the image is perceived. In contrast, referring to FIG. 4c, a target image is provided to a system with aberrations and a simulated version is captured by a camera to show the image as it is perceived. The difference between the two captured images provides insight as to the effectiveness of the system according to the present disclosure.

Figure 5:
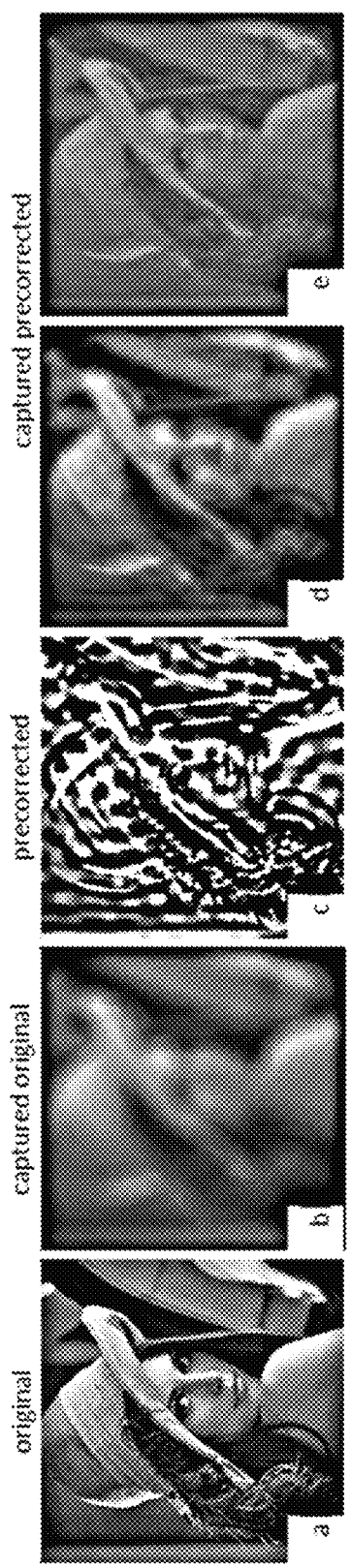
FIG. 5 is a schematic representation of a picture provided in an original target image, a calculated blurred image of an optical system with an aberration of the target image, a precorrection of the target image based on the teachings of the present disclosure, a calculated image of the optical system with the aberration of the precorrected image, and a captured image by a camera of the precorrected image.
Figure 6:
FIG. 6 represents schematic representations of a picture with multiple levels of ringing with the associated convolutions of the precorrected images.

Referring to FIG. 5, a pipeline of image processing is provided which demonstrates a visual summary of the system according to the present disclosure. The target image is identified as the original. A person with myopia (i.e., nearsightedness) observes the target image and perceives an image similar to the second image identified as captured original. The techniques described herein are based on a bounded total variation deconvolution method which carefully controls the process of creating a precorrected image as provided in the third image identified as precorrected directly in the available displayable range that when observed appears sharper (e.g., the fourth image from the left at high contrast and the fifth image from the left at medium contrast) than directly viewing the target image (i.e., the second image from the left identified as the captured original). FIG. 6 shows similar content but for human observation (as used by a user study) at three levels of ringing.

The refractive ability of the observer can be modeled by a point-spread-function (PSF). The method described herein supports, but is not restricted to, bounded deconvolution using total variation and to PSFs created using Zernike polynomials which are widely-used in ophthalmology to model optical aberrations. Since one can only have positive and bounded pixel values on a display, deconvolution-based methods are known to produce annoying visual ringing artifacts (i.e., unwanted intensity oscillations) in the computed image. The disclosed method uses bounded deconvolution to ensure pixel values are directly optimized in the [0.0, 1.0] range and introduces a new term, called relative total variation, which enables controlling the tradeoff of ringing-reduction vs. contrast gain. In practice, the method can produce images with relatively high contrast and little ringing.

The approach according to the present disclosure is used to yield improved sharp imagery in (i) synthetic simulations, (ii) physical setups of premeasured lenses inserted between a camera and either a standard computer display or a printed sheet of paper, (iii) captured images of physical scenes where objects are altered to have their precorrected appearances by the use of projectors, and (iv) under human observation.

That is, in various implementations described herein, but not limited to, the present techniques can provide personalized precorrected images, which upon observation by an individual exhibit sharper edges and higher contrast as compared to observing the original unprocessed images; improvements are obtained both for individuals with refractive errors as well as those with normal/corrected vision. Moreover, the techniques can provide a novel relative TV term for controlling the tradeoff of ringing-reduction versus contrast gain in the precorrected images. Further still, the techniques can provide a closed-loop automatic algorithm for effective PSF estimation and precorrected image calculation.

Some computational concerns for the disclosed method include the following.

Stability:

Inverting a convolution operator is highly sensitive to small amounts of noise in the image or in the PSF. The modulation transfer function (MTF) may contain zeroes or very small values, lending to unstable deconvolution and noisy results. Because of this instability, deconvolution is an ill-conditioned operation and may introduce strong visual artifacts in the resulting images.

Non-Negativity and Bounded Values:

Since one ultimate goal is to display an image, its pixel values are to be constrained to be limited by the minimum and maximum intensity of the display or by the minimum and maximum amount of light that can be reflected off a printed precorrected image. Enforcing this constraint tends to exacerbate ringing effects (which is mitigated by the relative total variation term).

Post-Deconvolution Sensitivity:

A precorrected image will be seen by a human eye, which is very sensitive to ringing artifacts. Referring to FIG. 6, three pairs (rows) of precorrected and convolved precorrected images are provided. Each row has a precorrected image with a different amount of ringing. Thus, the present techniques control the level of ringing in the precorrected image, beyond merely inspecting the sharpness of synthetically convolved precorrected images. Such control is achieved by providing at least one parameter 104 as depicted in FIG. 4a.

One of the ways the presented disclosure addresses the aforementioned concerns is by using a bounded total variation method. By considering the problem as a bounded deconvolution from the beginning, an optimal precorrected image with bounded pixel values is developed.

Optical System:

Examples of an optical system include, but are not limited to, a physical optical system, a human visual system, a mathematical optical model, a photographic camera, a photographic video camera, a computer-implemented machine having an image or video detection system, or combinations thereof. The optical system may generate a lower quality image, including but not limited to aspects such as less-sharp, blurry, and/or out-of-focus images. In addition, the optical system takes into account visual aberrations, including those involving myopia, hyperopia, presbyopia, astigmatism, coma, trefoil, spherical aberrations, and combinations thereof. It also may include monocular optics, binocular optics, and multi-ocular optics.

For the image formation process within the human eye, light from the exterior world goes through the cornea, aqueous humour, lens, and interior of the eye, until reaching the retina. FIG. 7a shows a conceptual simplification of this process using a thin-lens. If an object is too far (or too near) for a person to visually resolve its details, it appears blurred because the focal point is not on the retina. For example, a myopic person (i.e., nearsighted) focuses distant objects at a point in front of the retina (e.g., retina in FIG. 7a). The opposite occurs with hyperopia (i.e., farsightedness). For astigmatism, the eye has different focal points for different meridians. Other aberrations, such Keratoconus and cataracts, occur due to a combination of additional factors.

In the case of a person with normal vision, light coming from afar comes to a point of focus on the retina. For details near the limit of standard visual acuity (i.e., 1 arc minute at 20 ft or 6 m), some blurring still occurs in practice.

Convolution:

Although human focusing is complex, spatially-variant, and distance dependent, the perceived blur can be well modeled by convolving a 2D PSF with the target image. The following function simulates a prescribed amount of defocus $$b = K(t), \tag{1}$$

where $K(t) = K*t$ (i.e., the convolution of the in-focus target image t with the kernel K that represents the eye's PSF), and b is the convolved version of the target image. The terminology "convolved image" is used for pictures computed with a numerical simulation and "captured image" for pictures acquired by a camera. The PSF is defined by the observer's aperture (i.e., pupil size) and refractive behavior. For typical color images, Equation (1) is evaluated once for each of the three color channels.

An individual's PSF can be modeled by using Zernike polynomials, well-known to a person having ordinary skill in the art. In the implementation according to the present disclosure, second-order Zernike polynomials (i.e., $Z_2^{-2}$, $Z_2^0$, and $Z_2^2$) are used which are able to capture defocus and astigmatism aberrations. Although Zernike polynomials are used, the method according to the present disclosure is not dependent on any particular PSF formulation or equation set—thus it can be used with other PSF representations and with Zernike polynomials of higher order.

Precorrection:

The objective of precorrection is to generate an image that when observed appears sharper than directly observing the target image t. $K^{-1}(t)$ is defined as the desired deconvolution function applied to the target image with the expected PSF. Then, the optimal precorrected image p* (a theoretical intermediate image) and optimal convolved precorrected image q* is defined as $$p^* = K^{-1}(t) \quad (2)$$

and $$q^* = K(K^{-1}(t)). \quad (3)$$

The present techniques compute a precorrected image p that is as close as possible to the aforementioned p* and thus leads to an image q similar to q*.

A total-variation-based deconvolution method is used to calculate a precorrected image that upon observation appears sharper than looking at the target image. The solution also has no more than a user-specified amount of ringing and the user-defined (usually maximum) contrast ratio. A precorrected image calculated by the approach according to the present disclosure is denoted by $p = p(\theta, t_c)$ and is defined as $$p(\theta, t_c) = \arg\min_{0 \le \|p\|_\infty \le 1}(\|k^*p - t_c\|_{L2} + \theta T_v(p)), \quad (4)$$

Where $\theta \ge 0$ is a regularization weight;
K*p is the optimal convolved precorrected image; and
the regularization term $T_v(p) = \|\nabla p\|_{L1}$. The term $\|\nabla p\|_{L1}$ denotes the L1 norm of the gradient vector field of p defined as $$\|\Delta p\|_{L1} = \int\int \sqrt{\left(\frac{\partial p}{\partial x}\right)^2 + \left(\frac{\partial p}{\partial y}\right)^2} \, dx\,dy \quad (5)$$

The goal is to minimize $p(\theta, c)$ which is a measure of error between the precorrected image processed by the optical system and target image. The first term in equation (4) corresponds to the error component due to the deconvolution, while the second component corresponds to bounded TV component, as further described below.

Also in Equation (4), the variable $t_c = (t(c_H - c_L) + c_L)$ implies a rescaled version of the pixel values of the target image t to the contrast range $[c_L, c_H]$ for $0 \le c_L$, $c_H \le 1$ (note: $t_c = t$ for $c_L = 0$, $c_H = 1$).

To find a precorrected image p as close as possible to p*, the method according to the present disclosure has two logical components. The first component searches for the target-image contrast-range $[c_H - c_L]$ that can produce a precorrected image with no more than the specified amount of acceptable ringing. To quantify this, a parameter called relative total variation $\tau = \tau(p, t_c)$ is used which measures the additional amount of ringing in the precorrected image p as compared to the target image $t_c$. $\tau$ is defined by $$\tau(p, t_c) = \frac{\|\nabla p\|_{L1} - \|\nabla t_c\|_{L1}}{\|\nabla t_c\|_{L1}} \quad (6)$$

Hence, given $t_c$ and a user-specified value $\tau^*$, the first component seeks a precorrected image satisfying $$|\tau(p, t_c) - \tau^*| \le \epsilon. \quad (7)$$

If a solution cannot be found (i.e., the minimum value of the left side of Equation (7) is not less than or equal to $\epsilon$), it implies that the desired amount of ringing does not occur at the specified contrast range. Thus, the contrast range is reduced until the inequality is met. Since the contrast range can ultimately be reduced up to $c_L = c_H$ (e.g., a solid gray image), this process converges for reasonable values of $\tau^*$; in practice, $2 \le \tau^* \le 50$. Below the concept of relative total variation is described in more detail.

The second component of equation (4) (i.e., $\theta T_v(p)$) attempts to find that precorrected image $p(\theta, t_c)$ via a bounded total variation deconvolution. The deconvolution optimization includes a regularization weight $\theta \ge 0$ that is inversely proportional to the level of ringing in the computed precorrected image. Given $t_c$, a search algorithm (e.g., binary search) is used to find the $\theta$ value that is used to solve for $p(\theta, t_c)$ as in Equation (4) and that satisfies Equation (7). In practice, $\theta \in [0.0001, 0.2]$ was found to be a useful range: smaller values essentially ignored the regularization and larger values caused the image to be "washed out". The actual value of theta however is dependent on any additional normalization constants that might be used in Equation (4). Notice that in Equation (4) the pixel values of the solution p are constrained to the range [0.0, 1.0] so as to ensure any resulting precorrected image can be correctly displayed or printed. Moreover, the left term in Equation (4) ensures the convolved precorrected image is visually similar to the target image in an L2 sense, while the right term controls the ringing of the solution.

Relative Total Variation:

Relative TV measures the relative gain in total variation of the precorrected image as compared to the target image. The denominator in Equation (6) calculates the TV of a target image reduced to the contrast range $[c_L, c_H]$, and the numerator in Equation (6) is the difference between the TV of the precorrected image and of the target image with reduced contrast. Intuitively, as the contrast range of the target image is altered, a different amount of TV (i.e., ringing) is tolerable in the precorrected image and can thus perceive a similar result in the convolved precorrected image q. Moreover, by lowering the contrast level of the target image, the bounded pixel-value constraint effectively becomes less stringent, which in turn provides more freedom to form a sharper q—this agrees with the effect seen in the prior art techniques where lower contrast target images are able to be seen with improved sharpness. It should be noted that other prior art techniques also use a relative TV term for an application of TV, but with a different definition and purpose.

Figure 8:
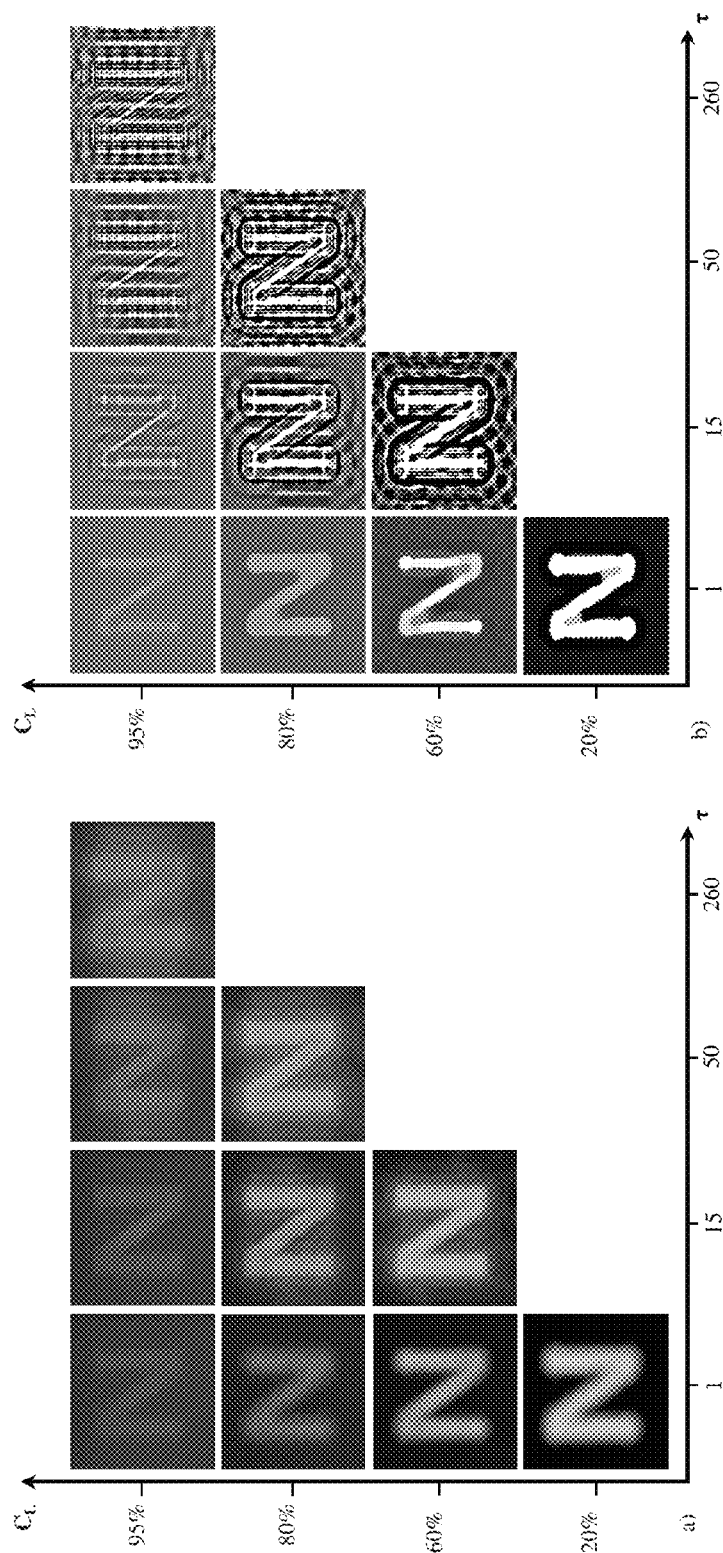
FIG. 8 represents two arrays of images depicting various convolved precorrected and precorrected images at different contrast levels.

FIG. 8 shows two arrays of images depicting various convolved precorrected and precorrected images at different contrast levels. All images have as the target image a sharp solid letter 'N' placed in the middle of the image. The right image array shows several versions of the precorrected image p. The left image array shows the corresponding convolved precorrected images, all using the same Zernike-based PSF. Within each array, the contrast range decreases with the vertical axis and ringing increases with the horizontal axis. The labels on the horizontal axis show the approximate values of τ. As expected, the amount of perceived ringing is about the same along each column.

For any contrast range, the details of the convolved precorrected image increases with relative TV as well as ringing and additional artifacts in the image. There is a value for the relative TV that corresponds to an optimal balance of ringing and sharpness. This optimal value depends on the inherent characteristics of the image.

In the exemplary embodiment of the system, the desired value τ* is selected by the user. Without loss of generality, it may be calculated by an external process as well. Empirically, for text images a larger relative TV is acceptable since the simple image content can afford it. For a busy color image, smaller values of τ* are preferred, and any introduced ringing is very distracting. The user study provides feedback about the visual tolerance of ringing for human observers.

The right part of Equation (4) is the regularization term $$T_v(p) = \|\nabla p\|_{L1} \quad (8)$$

that represents the total variation of the precorrected image p. As expected, this regularization term allows us to control ringing. A less obvious observation is that it also serves to enforce sharp edges in the convolved precorrected image q.

Ringing Control of Precorrected Image:

An example is provided to illustrate how the regularization term (8) controls ringing in the precorrected image. FIG. 7c depicts a portion of a 1D step signal with a sharp edge and an intensity difference of h. Given s as the observed slope in FIG. 7d, the signal is approximated by a function t(x) that is 0 for x≤a, sx for a≤x≤b, and bs for x≥b. The magnitude of the total variation of t is $$\|\nabla t(x)\|_{L1} = \int_a^b s\, dx = h. \quad (9)$$

where x is the integration variable. Note that the result is independent of a and b; it only depends on the magnitude of the single occurrence of a height difference. To visualize what happens when there is more ringing, FIG. 7d shows an original (target) and precorrected image pair (as an image and as a 1D slice of an image). It can be observed that the amount of ringing in the precorrected image is roughly "three times" that in the target image. Moreover, using the graph, the total variation can be computed to be about $\|\nabla p\|_{L1} = 3h$. Hence, this regularization term seems to be a good indicator of the amount of ringing and can be used to control it during deconvolution.

Edge Sharpening of Convolved Precorrected:

It is desirable, in some instances if not most, that the convolved precorrected image q (i.e., the observation by the viewer) presents sharp edges. Upon close inspection, the ringing in q is due to the instability of deconvolution (e.g., the difficulty inherent in approximating a signal with sharp edges by a finite series of continuous waves), the bound constraints, and Gibbs phenomenon. In particular, Gibbs phenomenon may demonstrate itself as oscillations that decay away from an edge. Hence, a consequence of Gibbs phenomenon is that ringing is stronger near edges of q. Thus, the areas where ringing occurs are also precisely where edge sharpness is most desired. Within the context of the total variation optimization of Equation (4), the tentative regularization term $$T_v(p)' = \|\nabla(k*p)\|_{L1} = \|\nabla q\|_{L1} \quad (10)$$

would reduce ringing in q and thus would also encourage edge sharpness.

Ringing Controls Sharpening. The effect of Equation (10) can in fact also be accomplished by using Equation (8). In particular, Equation (10) is bounded by the product of the L1 norm of the PSF kernel k and the total variation of the precorrected image p, i.e., $$\|\nabla q\|_{L1} \leq \sqrt{2} \|k\|_{L1} \|\nabla p\|_{L1}. \quad (11)$$

Since the L1 norm of the PSF k is typically normalized to 1, this inequality implies that if the ringing in p is reduced then sharpness in q is also improved. It is worth noting that the reverse inequality of (11) is not true in general (e.g. for k with small L1 norm).

To prove inequality (11), two points are provided. First, given that $\nabla(k*p) = k*\nabla p$, Young's inequality tells us $$\|\nabla(k*p)\|_{L1} \leq \|k\|_{L1} \|\nabla p\|_{L1}. \quad (12)$$

Second, the following inequalities are used $$\sqrt{\|u\|^2 + \|v\|^2} \leq \|u\| + \|v\| \leq \sqrt{2}\sqrt{\|u\|^2 + \|v\|^2}, \quad (13)$$

for u and v vectors in a normed space. These inequalities can be verified by squaring them.

Using Equations (12-13), the following inequalities are presented:

$$\|\nabla(k*p)\|_{L1} \leq \left\|k*\frac{\partial p}{\partial x}\right\|_{L1} + \left\|k*\frac{\partial p}{\partial y}\right\|_{L1} \leq \sqrt{2}\|k\|_{L1}\|\nabla p\|_{L1} \quad (14)$$

These last inequalities prove (11). Thus, by using the regularization term (8) both ringing and edge sharpness are controlled.

Point Spread Functions:

The shape of the PSF has an obvious impact on the precorrection ability; however, a Zernike-based PSF and TV-based regularization can produce sharp edges despite having zero's in the corresponding MTF. A Gaussian-based PSF avoids zeros in the lower frequencies but omits the higher frequency components in Equation (4). In contrast, a Zernike-based PSF exhibits a wave-like form whose MTF has near zeros in the lower and higher frequencies but the higher frequencies are not completely omitted. Hence, since the TV-based regularization controls the undesired effects of near zeros in the MTF, the higher frequencies of the Zernike-based PSF are used despite the zeros.

An informal synthetic experiment was performed that optimizes the PSF shape. Using a fixed convolved target image b, the system optimized the shape of the PSF so as to maximize the sharpness of the convolved precorrected image. More precisely, p is recomputed and k altered so as to minimize Equation (4), subject to the additional constraint $\|k*t_c - b\|_{L2} \to 0$ for a fixed value of θ. The shape of k is altered by varying the control points of an interpolating spline that defines a circularly symmetric 2D PSF. For several images and amounts of blur, the optimization always converged to a PSF whose shape roughly mimicked the oscillating nature of Zernike-based PSFs and yielded a similar level of sharpness in the convolved precorrected image.

Figure 7B:
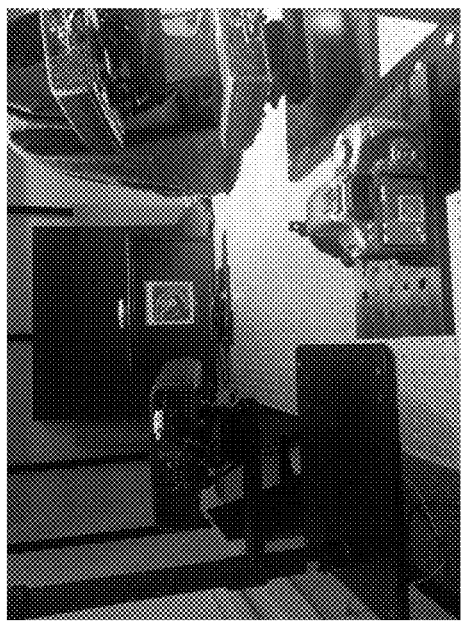
FIG. 7b represents an experimental setup of a premeasured lens placed in front of a digital camera in order to simulate a prescribed amount of positive or negative diopters of blur.
Figure 7A:
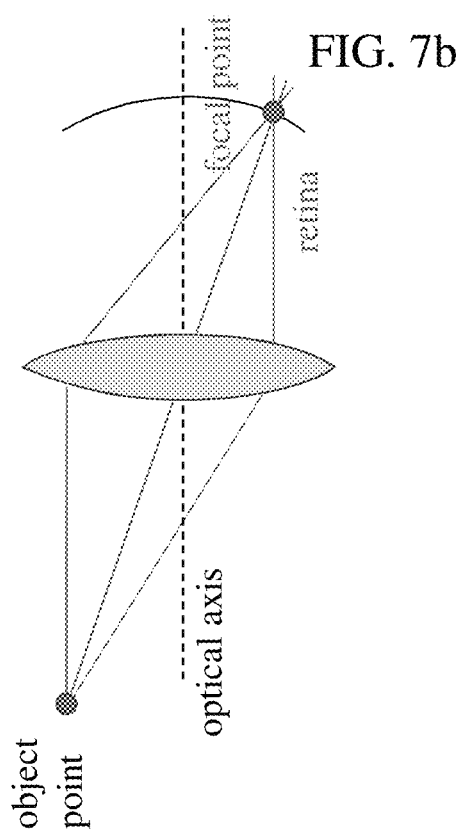
FIG. 7a represents a conceptual schematic of an optical system using a thin-lens.
Figure 7D:
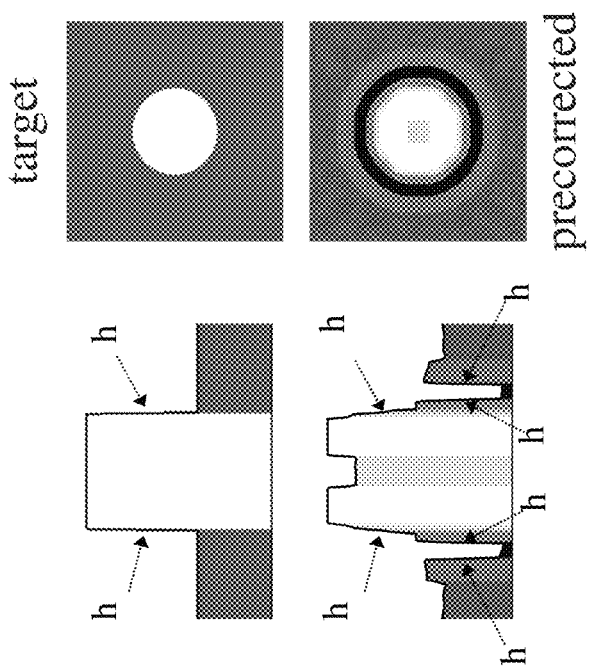
FIG. 7d represents an observation of the 1D step of FIG. 7C.
Figure 7C:
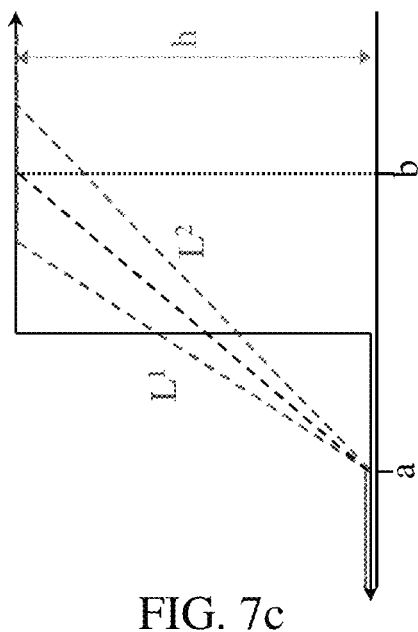
FIG. 7c is graph which depicts a portion of a 1D step signal with a sharp edge and an intensity difference of h.

Precorrection System:

In the following, an example automatic framework implementing the aforementioned precorrection computation for a given target image t and relative total variation τ* is provided. Different deployment system types are presented:

Camera-Screen System:

Color precorrected images are displayed on a standard computer screen or a printed sheet of paper; a premeasured lens is placed in front of a digital camera in order to simulate a prescribed amount of positive or negative diopters of blur (FIG. 7b);

Projector-Camera System:

Compensation images are projected on top of a colored physical object and the object is captured by a digital camera with a premeasured lens in front of it; the compensation images are such as to alter the visual appearance of the object to that of the precorrected color image's appearance.

Human Observation:

Precorrected color images are displayed on a computer screen or on a printed sheet of paper for human observation; this scenario was used for the user study.

For each system type, the framework estimates a suitable PSF, finds the largest contrast range for a desired relative TV, and then creates (and displays/prints) a precorrected image. The PSFs for the three system types are not identical—thus a precorrected image generated for the camera-screen system is not suitable for human viewing and vice versa.

PSF Parameter Estimation:

The first step is to obtain the Zernike-based PSF k of the optical system. The Zernike parameter values are obtained either directly (e.g., from the refractive corrective prescription of a person) or indirectly via an optimization. The latter is the case for the camera-screen and projector-camera system whereby a photographic camera observes a standard computer screen, a sheet of paper, or a physical scene. The camera, with an approximately known and fixed aperture, is focused on the content. Then, a refractive error is induced by placing a lens (or set of lenses) of known diopter immediately in front of the camera. As much of the camera processing machinery is disabled as possible and capture an image. Afterwards, an affine transformation is computed to best align the captured target image b to image t and estimate the Zernike parameter values to best reproduce the blur in the captured image.

Precorrection Calculation:

In the next step, the optimization described by Equations (4-7) is presented. Given a target image t, a desired $\tau^*$, and the estimated PSF, the optimization is provided using the following steps.

Contrast Level and $\theta$ Estimation:

First, the largest target-image contrast-range $[c_L, c_H]$ and corresponding $\theta$ are determined that can produce the precorrected image with the desired relative TV $\tau^*$. There are multiple ways to alter the contrast (e.g., increase/decrease one or both of $c_L$ and $c_H$. By default for white text on black, $c_L$ (and keep $c_H$ near 1) is determined and for busy color images $c_L$ is increased and $c_H$ is decreased. However, the user can select an alternative contrast reduction strategy. The method according to the present disclosure performs a binary search to find the smallest $\theta$ value that generates a relative TV close to the desired $\tau^*$ value. The chosen value for $\tau^*$ may not be feasible for the given image (i.e., inequality of Equation (7) cannot be met). In such cases, the method reduces the contrast range by a small amount and iterates until a solution is found.

PSF Tuning:

Second, once $\theta$ is calculated the precorrected image p and corresponding synthetically-computed $q=k*p$ are determined for a range of diopters and apertures near the estimated PSF values. Using a sharpness metric, from amongst these solutions (intermediate images) the precorrected image that yields the sharpest q is chosen. By this mechanism, a PSF shape is converged upon that may exhibit slightly better performance during precorrection.

The sharpness metric automatically measures the magnitude of high frequencies present near the edges of the target image. Using an edge filter (e.g., Canny), target image pixels near an edge are selected. Then, the magnitude of the frequencies in the Fourier transform of p that are above the median value are summed together. The computed sum is returned as the value of the sharpness metric for the entire image.

The method according to the present disclosure is stable under lateral and some distance displacement of the viewer which makes the deployment (e.g., on paper) particularly attractive.

Ringing and Contrast Tradeoff:

The approach according to the present disclosure is able to trade ringing for contrast. The previous referred to FIG. 8 shows various captured images of the letter 'N'. For each image, the contrast range $[c_L, c_H]$ and relative TV are altered. Along the horizontal axis, $\tau$ increases from 1 (i.e., little ringing) to 260 (i.e., high ringing). Each column has a similar amount of ringing, demonstrating that $\tau$ is a good variable for measuring it. As $\tau$ is increased, sharpness increases as well as ringing. In this example, a balance of these tradeoffs occurs for a desired $\tau^*$ somewhere in between 15 and 50. When contrast is high, the method according to the present disclosure does not necessarily have room to increase $\tau$ to $\tau^*$. Therefore, contrast is decreased until a precorrected image with relative TV equal to $\tau^*$ is achieved. Nevertheless, it is not possible to achieve all $\tau^*$ for all contrast levels (i.e., images corresponding to bottom right triangle of the table are not possible). Thus, image sharpness is increased at the expense of reduced contrast.

Figure 9:
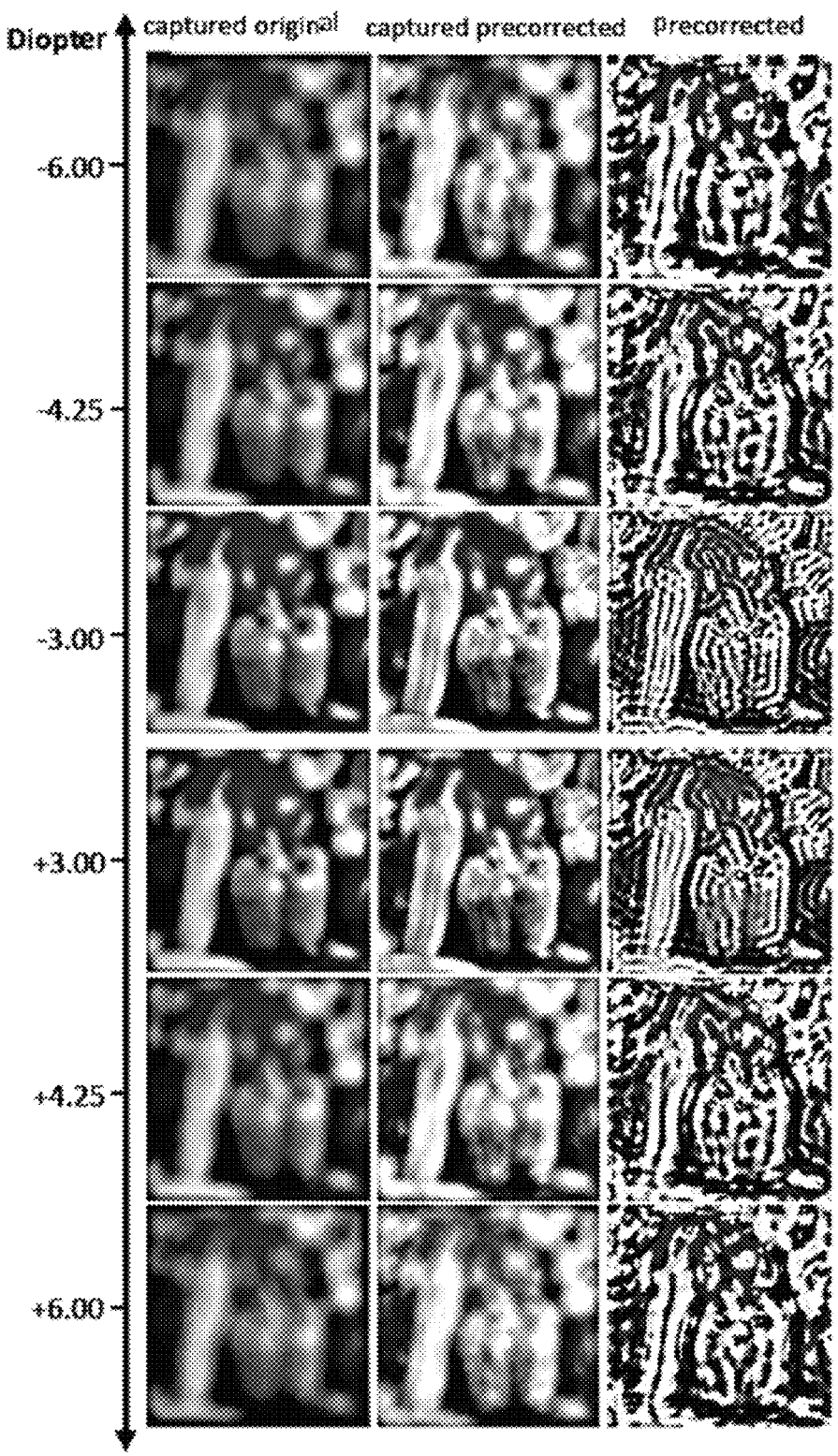
FIGS. 9 and 10 represent captured precorrected images for several refractive aberrations.
Figure 10:
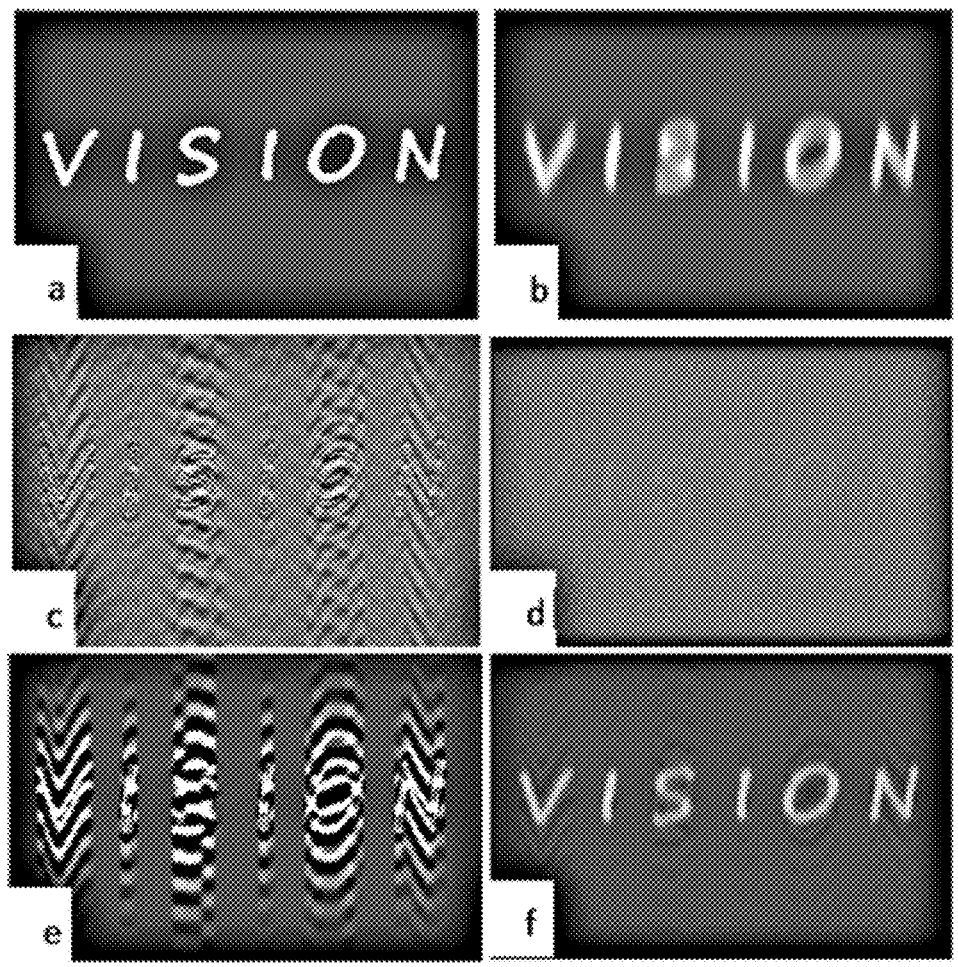

Different Refractive Errors:

FIGS. 9 and 10 show captured precorrected images for several refractive aberrations. In FIG. 9, images precorrected for −6 to +6 diopters are presented; e.g., potential corrective prescriptions for myopia, hyperopia, or presbyopia. Results for this amount of refraction have not been shown by any of the mentioned previous works. Some of the observed graininess is because the images in the left two columns are photographs of a computer screen showing the original or precorrected images, respectively. FIG. 10 shows an example of medium-range astigmatism and myopia. In all cases a clear improvement can be observed in sharpness and detail using the precorrected image. As diopters increase, resolving detail is more challenging because of the wider PSF.

Reading and Visual Acuity:

An important application of the algorithm is that it could be used to automatically customize text for reading by people with refractive errors. In FIG. 11, a portion of typical Snellen Chart is provided to estimate visual acuity. In the experiment the Snellen chart was positioned at 1.5 m and captured images with an induced blur of −5 D. A notable improvement is observed in visual acuity from 20/70 and downwards, making the 20/20 line almost clearly visible (bottom line of each image). The contrast loss is due to the initial reduction needed to achieve the desired total variation in the precorrected image. The results of a similar experiment provided in prior art presents images with less ringing artifacts but significantly lower contrast and requires a precisely calibrated viewer location and customized hardware.

Figure 12:
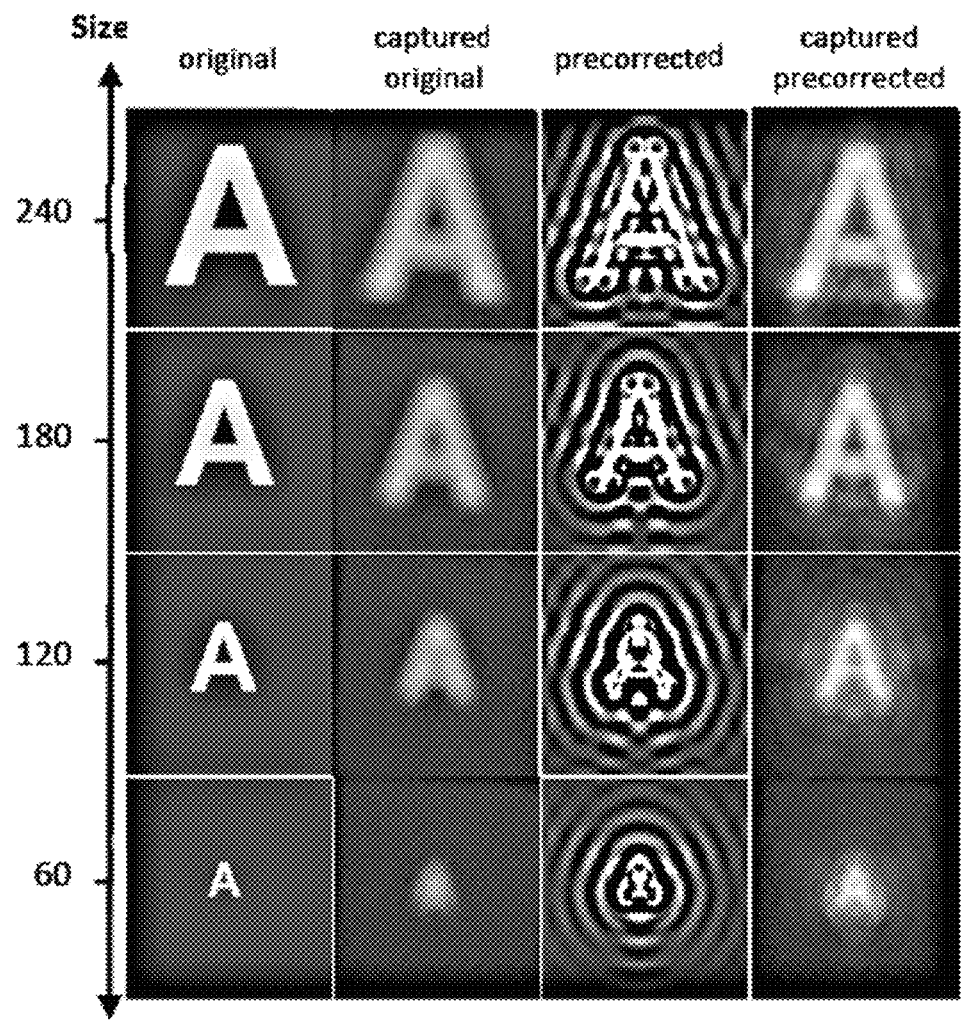
FIG. 12 represents appearance of a single letter at multiple sizes.

In FIG. 12, the appearance of a single letter at multiple sizes (or equivalently at different distances) is presented. Images of a letter at a distance of 1.5 m are captured with a blur of −5 D. When the letter is small (e.g., 60 pixels), the captured target image is unrecognizable. In contrast, the captured precorrected image shows a letter that begins to be distinguishable. As the font size increases, the captured precorrected image becomes readable sooner than the observation of the standard text. When the letter size is large (e.g., 240 pixels), both images are readable. Nevertheless, the precorrected images show an enhanced sharpness. Special font could be generated automatically using the algorithm so as to provide a better reading experience.

Figure 13:
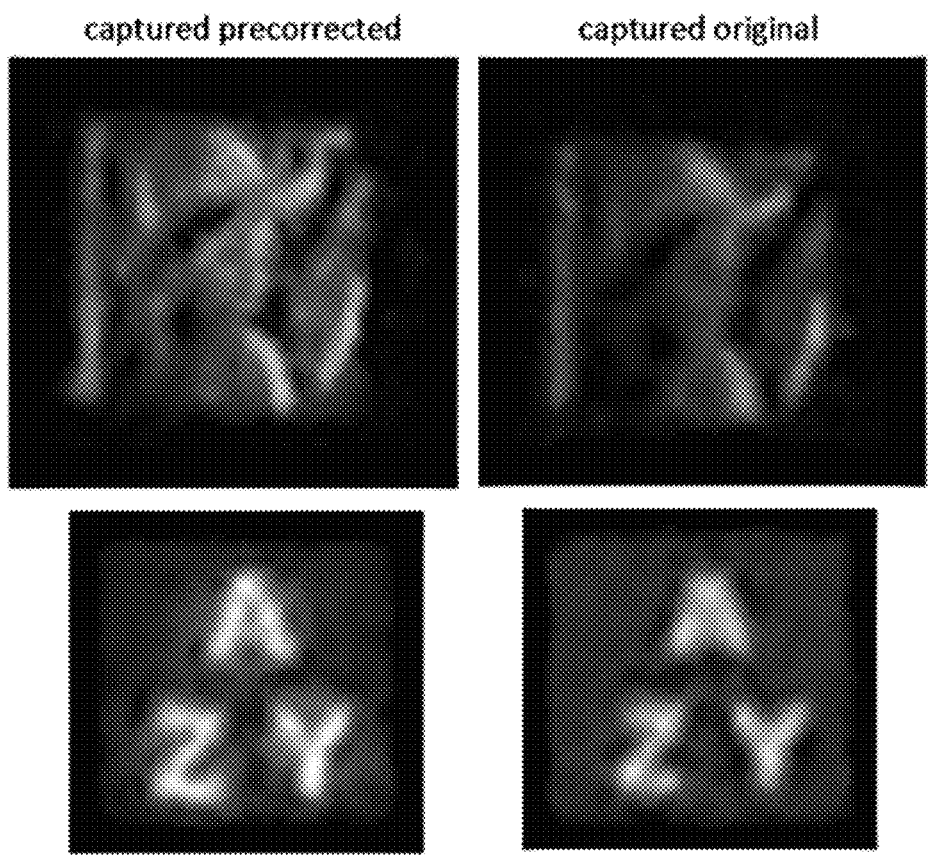
FIG. 13 represents comparison between small images captured by a camera that was focused on the content.

Distant and Small Content:

Another application for the present techniques is improving visual acuity for individuals with normal vision. The definition of standard visual acuity (i.e., the ability to recognize a letter of size 5 minutes of an arc at a distance of 1 meter) is used to model an individual with normal vision looking at distant objects. FIG. 13 shows the comparison between small images captured by a camera that was correctly focused on the content. The ability to recognize details in the images is improved by using the method.

Figure 14:
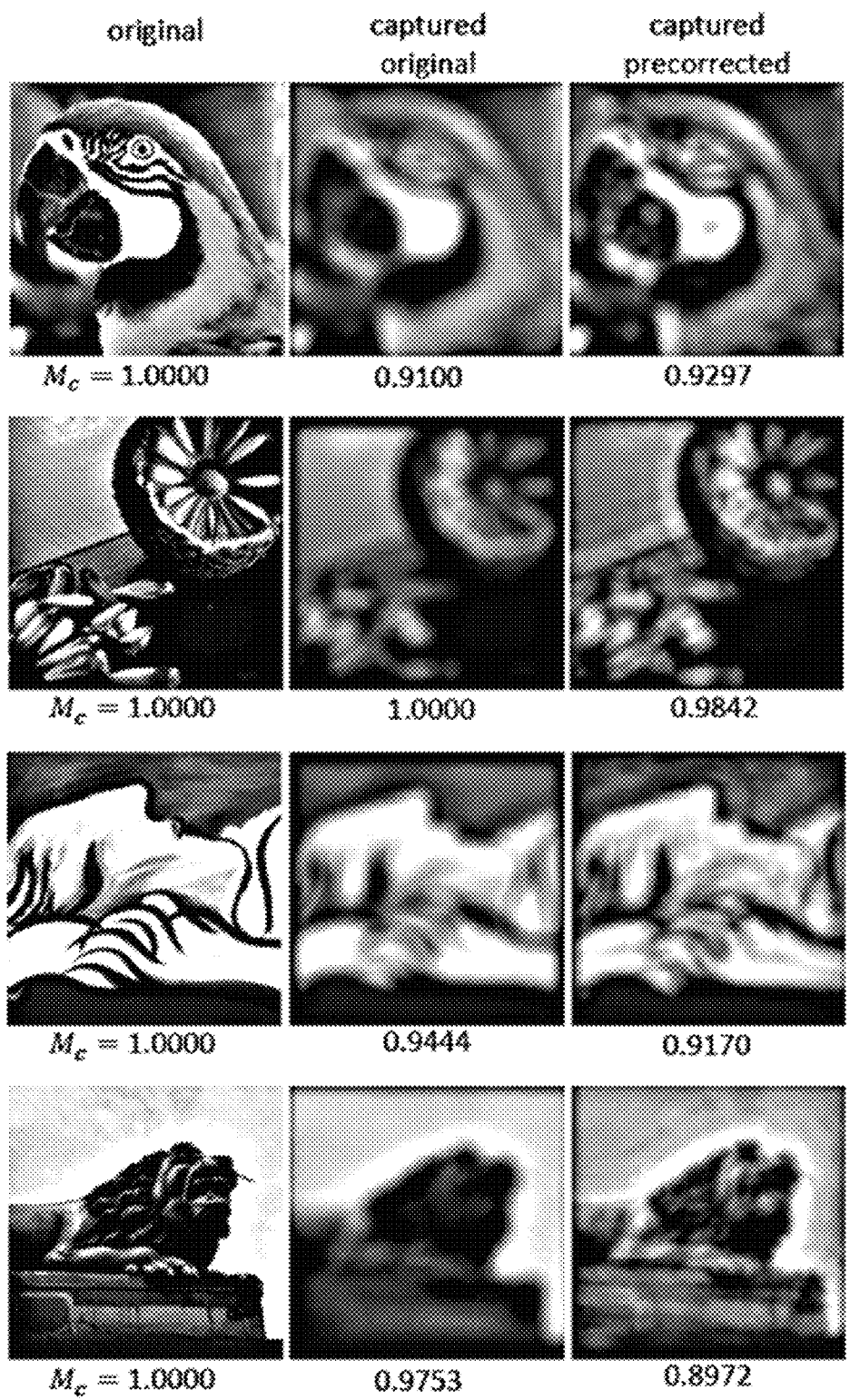
FIG. 14 represents several target images (original), captured target images (captured original), and captured precorrected images (captured precorrected) all under −4.75 D of refractive error at 1.5 m.

The present techniques work across any of a variety of image types and at high contrast. FIG. 14 shows several target images (original), the captured target images (captured original), and the captured precorrected images (captured precorrected) all under −4.75 D of refractive error at 1.5 m. The target images have maximum contrast ratio (i.e., minimum and maximum intensities are 0 and 1, respectively). The imagery shows noticeably improved sharpness at almost the same contrast as the target images. While the resulting image quality may still suffer from some artifacts, significantly higher contrast ranges are achieved which support higher diopters than others.

User Study

A user study was undertaken to evaluate the performance of an example implementation of the present techniques. The study consisted of 22 people (65% male, 35% female) with an average age of 28.3 years. Subjects were voluntarily recruited from a university campus. We performed five groups of tests. The test content was randomized wherever possible. For each test, subjects had normal vision and we induced −2.75 D of myopia by placing a lens in front of one eye (and covering the other eye).

Subjects stood 2.5 m from the display and viewed images of sizes ranging from 3 cm (for text) to 31 cm for the Lenna image. After a short explanation and calibration session (to find the optimal location for their individualized viewing), subjects were asked several questions and a response form was filled out for them. The following paragraphs provide a summary of these results.

Precorrected Vs. Original:

This first experiment wants to verify whether our method improves the perceived sharpness as compared to the original image. For this, we displayed side by side three pairs of images (one pair at a time): one precorrected and the original. We ordered them randomly to prevent bias. The conclusion is that subjects preferred observing a precorrected image over the standard original image. We use a Likert-scale (where −3 means "strongly prefer original image", −2 means"prefer original image", −1 means "slightly prefer original image", 0 means "similar", +1 means "slightly prefer our method", +2 means "prefer our method", and +3 means "strongly prefer our method") and the study resulted in a mean score (over all participants and images in this study) of 1.13 and confidence interval (0.48, 1.78), critical-t 2.09 and standard error of 0.31 (95% confidence interval). Moreover, 95% of the people selected at least one of our precorrected images over the original.

Displacement:

The second experiment seeks to evaluate the spatial robustness of our solution to displacement. For this, we asked subjects to move 0.5 m to the sides (left, right, front, and back) and to compare the perceived sharpness in comparison with the initial location. Moving laterally, 84.2% of the subjects claimed that this did not significantly affect image quality. Using a Likert-scale (where −2 means "much worse than center", −1 means "worse than center", 0 means "similar than center", +1 means "better than center", and +2 means "much better than center"), the mean value of the questionnaire responses for all participants was −0.052. Moving forward/backward, however, did result in increased sensitivity, with 48% of the subjects indicating moving forward or backward decreased image quality but with a mean value of just −0.11. We conclude that the displacement performed does not significantly affect solution quality.

Reading:

The third experiment tries to analyze whether our system improves readability. For this, we presented to the subjects in random order two different images of 3 cm tall text: one precorrected by our system and the corresponding original image, and ask them to read the letters. 82% of the people indicated it was easier to read our precorrected text image over the original text.

Contrast and Ringing Sensitivity:

This experiment analyzed whether the subjects would prefer to trade off contrast with more sharpness. For this, we displayed a set of 9 precorrected randomly placed images and asked the volunteers to rank them. The precorrected images presented three levels of contrast loss (20%/40%/60%) and three different $\tau$ (low/mid/high). All subjects choose as first option the least contrast loss (20%), and the largest cluster of same-respondents (45%) chose the middle $\tau$. This implies that humans prefer high contrast and suggests that either, lower or higher levels of ringing, are counterproductive.

Figure 2:
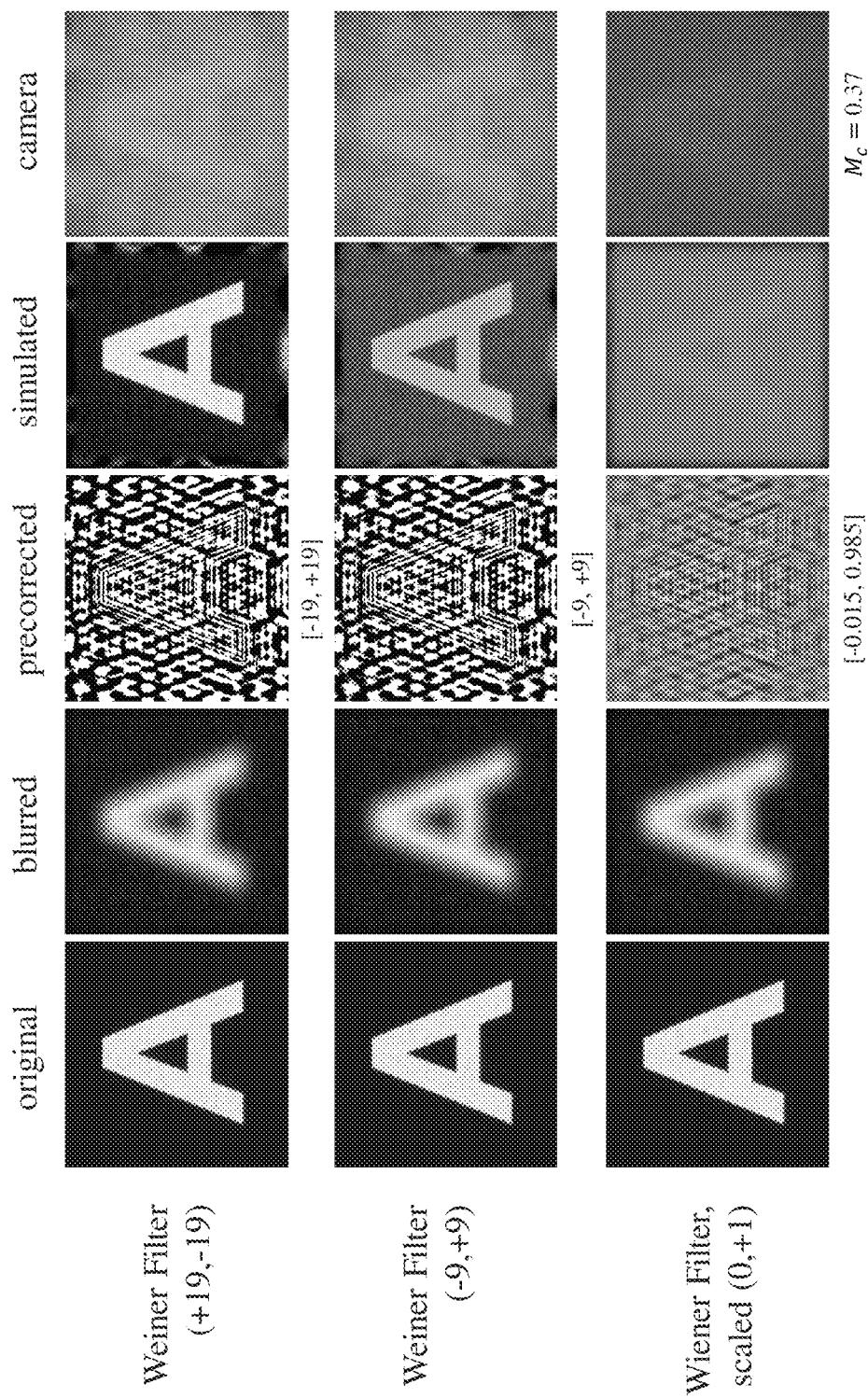
FIG. 2 is a schematic representation of the letter "A" as provided in original target images, calculated as blurred images of an optical system with an aberration of the target images, precorrection of the target images based on software approaches as provided in the prior art, calculated images of the optical system with the aberration of the precorrected images, and captured images by a camera of the precorrected images.

Comparison:

The last experiment wants to compare our system with a Wiener filter alternative. For this, we display the same text with three precorrections: one Wiener-filter based (3rd row of FIG. 2), one using inverse filtering, and one using our method. No subject preferred the inverse filtering. 95% of the subjects preferred our precorrected image and 5% chose the Wiener filtered image. Moreover, 86% could read our precorrected text while only 9% could read the Wiener-filtered image.

Figure 15B:
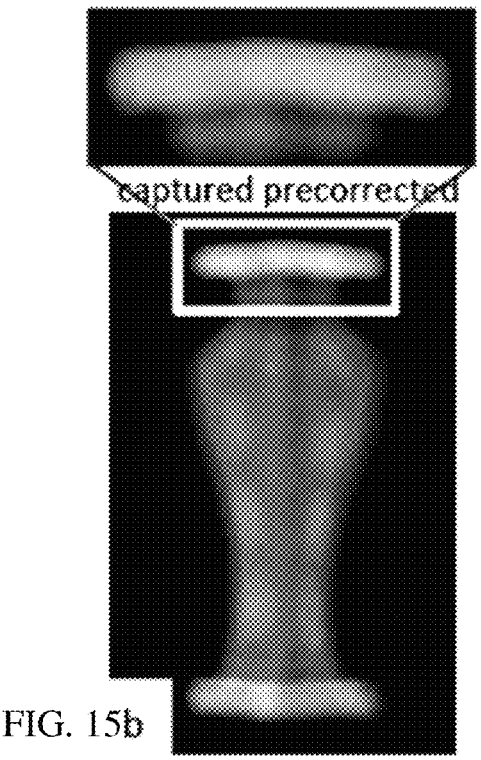
FIGS. 15a, 15b, and 15c represent an application of the present techniques to 3D scene precorrection.
Figure 15C:
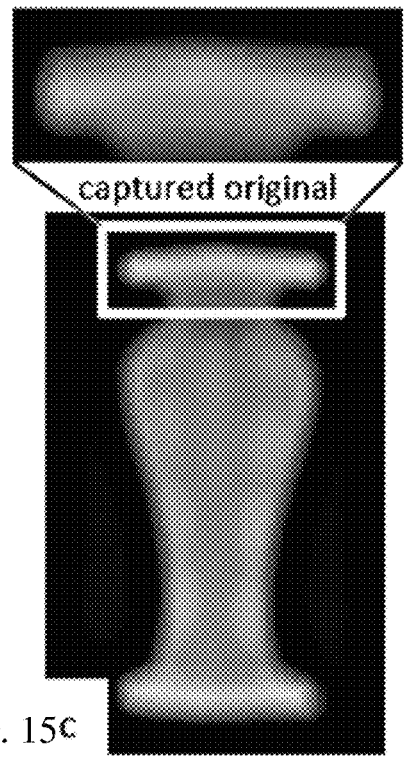
Figure 15A:
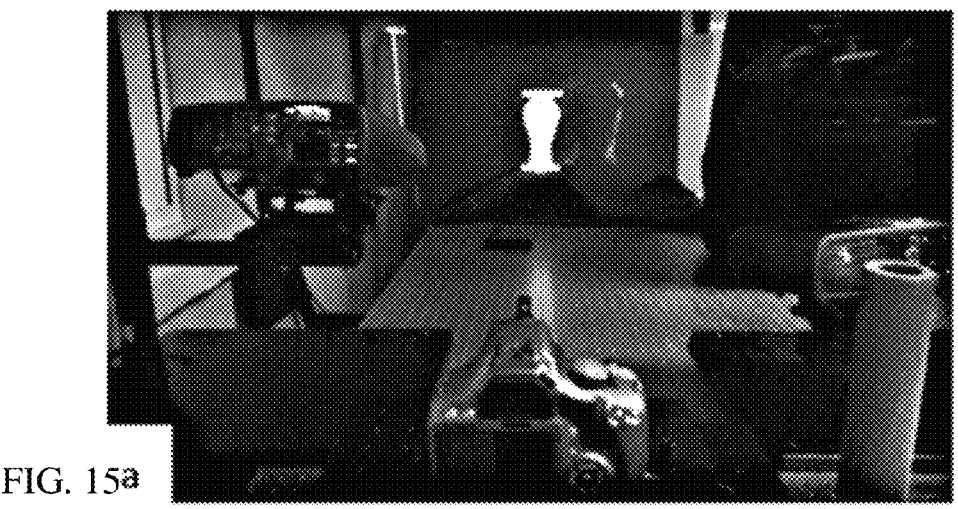

Example 3D Scene:

FIGS. 15a, 15b, and 15c show an implementation application of the present techniques to 3D scene precorrection. The target image of a 3D scene as seen from a digital camera was captured. Then, the target image was precorrected and used a projector-camera system to alter the appearance of the physical scene (e.g., object) to that of the precorrected image. Thus, when the scene from the point of view of the camera is observed, and with the same amount of refractive error, the scene appears sharper.

Thus the present techniques provide a bounded-based approach to improve the visual perception of images under refractive aberrations and under normal vision. The techniques can control ringing artifacts in the precorrected image while sharpening edges of the captured precorrected image, and by doing so sharp edges are recovered with high contrast. Further, the techniques can produce imagery preferred by humans as per the user study.

FIG. 16 is an example block diagram 800 illustrating the various components used in implementing an example embodiment of the techniques discussed herein. An imaging processing device 802 may be coupled to an optical imager system 816 that collects optical images and optical data of a subject 820 in accordance with executing the functions of the disclosed embodiments. The imaging processing device 802 may have a controller 804 operatively connected to the database 814 via a link connected to an input/output (I/O) circuit 812. It should be noted that, while not shown, additional databases may be linked to the controller 804 in a known manner. The controller 804 includes a program memory 806, the processor 808 (may be called a microcontroller or a microprocessor), a random-access memory (RAM) 810, and the input/output (I/O) circuit 812, all of which are interconnected via an address/data bus 820. It should be appreciated that although only one microprocessor 808 is shown, the controller 804 may include multiple microprocessors 808. Similarly, the memory of the controller 804 may include multiple RAMs 810 and multiple program memories 806. Although the I/O circuit 812 is shown as a single block, it should be appreciated that the I/O circuit 812 may include a number of different types of I/O circuits. The RAM(s) 810 and the program memories 806 may be implemented as semiconductor memories, magnetically readable memories, and/or optically readable memories, for example. A link 824 may operatively connect the controller 804 to the optical imager system 816, through the I/O circuit 812, and assuming the imager system 816 has converted the optical collected image data into electrical signal data.

The program memory 806 and/or the RAM 810 may store various applications (i.e., machine readable instructions) for execution by the microprocessor 808. For example, an operating system 830 may generally control the operation of the imaging processing device 802 and provide a user interface to the imaging processing device 802 to implement the processes described herein. The program memory 806 and/or the RAM 810 may also store a variety of subroutines 832 for accessing specific functions of the imaging processing device 802. By way of example, and without limitation, the subroutines 832 may include, among other things: a subroutine for taking measurements with the optical system 816 and other subroutines, for example, implementing software keyboard functionality, interfacing with other hardware in the imaging processing device 802, etc. The program memory 806 and/or the RAM 810 may further store data related to the configuration and/or operation of the imaging processing device 802, and/or related to the operation of one or more subroutines 832. For example, the data may be data gathered by the optical image system 816, data determined and/or calculated by the processor 808, etc. In addition to the controller 804, the imaging processing device 802 may include other hardware resources. The imaging processing device 802 may also include various types of input/output hardware such as a visual display 826 and input device(s) 828 (e.g., keypad, keyboard, etc.). In an embodiment, the display 826 is touch-sensitive, and may cooperate with a software keyboard routine as one of the software routines 832 to accept user input. It may be advantageous for the imaging processing device to communicate with a broader network (not shown) through any of a number of known networking devices and techniques (e.g., through a computer network such as an intranet, the Internet, etc.). For example, the imaging processing device may be connected to an imaging database, image or video projection system, etc. Accordingly, the disclosed embodiments may be used as part of an automated closed loop system or as part of an optical correction system.

The techniques described herein may be implemented in software using one of many available programming languages and environments. It may also be implemented in higher-level prototyping environments (e.g., MATLAB). To produce color images, precorrection per channel is carried out. Then, a single RGB image to display or print is assembled. When displaying images, the physical size of the pixels is taken into account.

The present techniques may be implemented as routines, subroutines, applications, or instructions. They may be implemented in software (e.g., code embodied on a machine-readable medium or in a transmission signal), hardware, or some combination. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

In addition, unless specifically stated otherwise: as used herein, "dynamic range" and "contrast" are used interchangeably. The phrase "target image" appearing in various places in the specification is meant to be interchangeable with the phrase "original image." Similarly, the phrase "output image" appearing in various places in the specification is interchangeable with the phrase "precorrected image".

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

Figure 17:
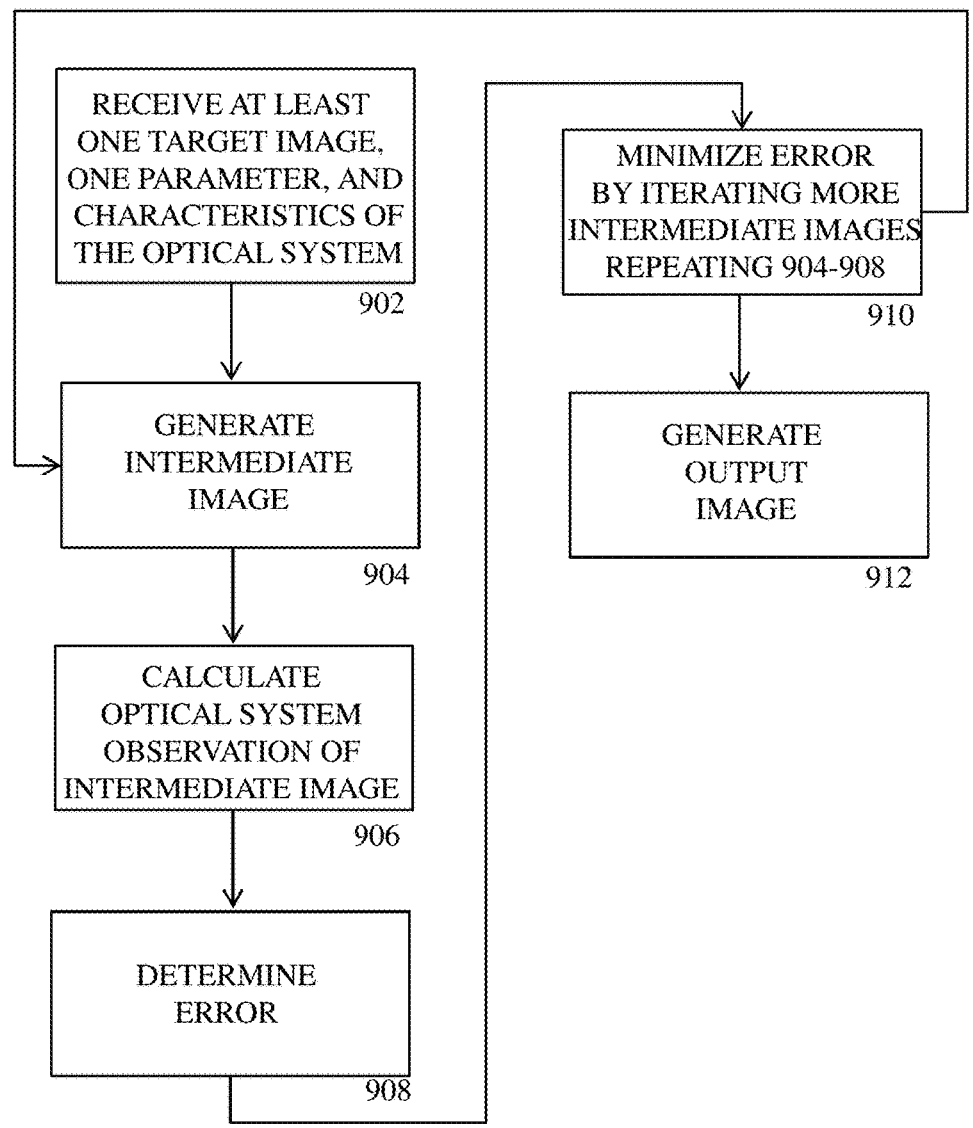
FIG. 17 is a flow chart depicting steps of a method as described herein.

Referring to FIG. 17 a flowchart of a method according to the present disclosure is provided. The flowchart begins at step 902 by receiving at least one target image and at least one parameter, and optionally characteristics of the optical system. Next at step 904 an intermediate image is calculated. Next at step 906, an optical system observation of the intermediate image is calculated. Next at step 908, the calculation is compared to the target image to determine an error. Next at step 910, the error is minimized by iterating steps 904-908 by altering the intermediate images until the error has reached a minimum threshold. Next at step 912, an output image is generated.

Those skilled in the art will recognize that numerous modifications can be made to the specific implementations described above. The implementations should not be limited to the particular limitations described. Other implementations may be possible.

What is claimed:

1. A method to generate an output image that improves observation of a target image viewed on a medium by an optical system, comprising:
 receiving at least one target image by a processing system;
 receiving one or more characteristics associated with the optical system defining a point spread function of a subject's ocular system including an optical transfer function;
 receiving at least one parameter by the processing system associated with the desired output image;
 defining an error signal associated with the difference between calculated optical system observation of intermediate images that are generated by the processing system and the at least one target image, where a first intermediate image is generated based on a Bounded Total Variation deconvolution that is based on the one or more characteristics associated with the optical system and the at least one parameter;
 minimizing the error signal by altering the intermediate images based on changes to one or more characteristics associated with the intermediate images and the at least one parameter, resulting in an intermediate image associated with an error at or below a threshold; and generating an output image associated with the intermediate image having the minimized error.

2. The method of claim 1, wherein the at least one parameter includes user-selectable amount of ringing associated with image intensity oscillations surrounding contours of the at least one target image, an amount of the desired visual sharpness of the output image, an amount of dynamic range of intermediate images or the output image, and combinations thereof.

3. The method of claim 1, wherein the at least one target image, the intermediate images, and the output image comprise images, video, font, visual digital content, and combinations thereof, each including at least one channel of information.

4. The method of claim 1, the medium comprises an electronic display device, printed media, physical surfaces, projection onto a physical surface, and combinations thereof.

5. The method of claim 2, the at least one parameter is associated with one or more parts of the at least one target image, the intermediate images, and the output image.

6. The method of claim 1, the optical system further comprises a physical optical system, a human visual system, a mathematical optical model, a photographic camera, a photographic video camera, a computer-implemented machine having an image or video detection system, and combinations thereof.

7. The method of claim 1, the optical system includes visual aberrations, comprising myopia, hyperopia, presbyopia, astigmatism, coma, trefoil, spherical aberration, and combinations thereof.

8. The method of claim 1, the sizes of the intermediate images are substantially the same as the image sizes of the at least one target image.

9. The method of claim 1, the one or more characteristics associated with the optical system is determined based on a Zernike polynomial.

10. An image improvement system, comprising:

an input channel configured to receive at least one target image;

a processor configured to receive the at least one target image by a processing system, receive one or more characteristics associated with the optical system defining a point spread function of a subject's ocular system including an optical transfer function;

receive at least one parameter by the processing system associated with the desired output image, define an error signal associated with the difference between calculated optical system observation of intermediate images that are generated by the processing system and the at least one target image, where a first intermediate image is generated based on a Bounded Total Variation deconvolution that is based on the one or more characteristics associated with the optical system and the at least one parameter, minimize the error signal by altering the intermediate images based on changes to one or more characteristics associated with the intermediate images and the at least one parameter, resulting in an intermediate image associated with an error at or below a threshold, and generate an output image associated with the intermediate image having the minimized error, and an output channel configure to output the output image.

11. The system of claim 10, wherein the at least one parameter includes user-selectable amount of ringing associated with image intensity oscillations surrounding contours of the at least one target image, an amount of the desired visual sharpness of the output image, an amount of dynamic range of intermediate images or the output image, and combinations thereof.

12. The system of claim 10, wherein the at least one target image, the intermediate images, and the output image comprise images, video, font, visual digital content, and combinations thereof, each including at least one channel of information.

* * * * *